United States Patent
Krug

(10) Patent No.: US 10,324,086 B2
(45) Date of Patent: *Jun. 18, 2019

(54) MAGNETIC REMOVAL OR IDENTIFICATION OF DAMAGED OR COMPROMISED CELLS OR CELLULAR STRUCTURES

(71) Applicant: Inguran, LLC, Navasota, TX (US)

(72) Inventor: Kristie Krug, Upper Arlington, OH (US)

(73) Assignee: Inguran, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/713,391

(22) Filed: Sep. 22, 2017

(65) Prior Publication Data

US 2018/0045718 A1 Feb. 15, 2018

Related U.S. Application Data

(63) Continuation of application No. 13/974,139, filed on Aug. 23, 2013, now Pat. No. 9,804,153.

(60) Provisional application No. 61/694,756, filed on Aug. 29, 2012.

(51) Int. Cl.
| | |
|---|---|
| *B03C 1/28* | (2006.01) |
| *G01N 33/543* | (2006.01) |
| *G01N 33/569* | (2006.01) |
| *C12N 13/00* | (2006.01) |
| *B03C 1/01* | (2006.01) |
| *B03C 1/015* | (2006.01) |
| *B03C 1/02* | (2006.01) |
| *B03C 1/023* | (2006.01) |

(52) U.S. Cl.
CPC .......... *G01N 33/5434* (2013.01); *B03C 1/01* (2013.01); *B03C 1/015* (2013.01); *B03C 1/02* (2013.01); *B03C 1/023* (2013.01); *B03C 1/288* (2013.01); *C12N 13/00* (2013.01); *G01N 33/54346* (2013.01); *G01N 33/54353* (2013.01); *G01N 33/56966* (2013.01); *B03C 2201/18* (2013.01); *B03C 2201/26* (2013.01)

(58) Field of Classification Search
CPC ......... G01N 33/5434; G01N 33/56966; G01N 33/54346; G01N 33/54353; B03C 1/01; B03C 1/288; B03C 1/015; B03C 1/02; B03C 1/023; B03C 2201/18; B03C 2201/26; C12N 13/00
See application file for complete search history.

(56) References Cited

U.S. PATENT DOCUMENTS

| | | | |
|---|---|---|---|
| 3,917,538 A | 11/1975 | Rosensweig | |
| 3,976,197 A | 8/1976 | Bhattacharya | |
| 4,083,957 A | 4/1978 | Lang | |
| 4,092,229 A | 5/1978 | Bhattacharya | |
| 4,276,139 A | 6/1981 | Lawson | |
| 4,554,088 A | 11/1985 | Whitehead et al. | |
| 4,698,302 A | 10/1987 | Whitehead et al. | |
| 4,927,749 A * | 5/1990 | Dorn | G01N 33/552 |
| | | | 424/529 |
| 5,466,574 A | 11/1995 | Liberti et al. | |
| 5,466,587 A | 11/1995 | Fitzpatrick-McElligott et al. | |
| 5,597,531 A | 1/1997 | Liberti et al. | |
| 6,153,373 A | 11/2000 | Benjamin et al. | |
| 7,169,548 B2 | 1/2007 | Chisholm et al. | |
| 7,699,979 B2 | 4/2010 | Li et al. | |
| 7,754,444 B2 | 7/2010 | Xu et al. | |
| 7,776,580 B2 | 8/2010 | Zhang et al. | |
| 7,829,350 B2 | 11/2010 | Josephson et al. | |
| 9,804,153 B2 * | 10/2017 | Krug | C12N 13/00 |
| 2002/0034537 A1 | 3/2002 | Schulze et al. | |
| 2002/0182751 A1 | 12/2002 | Herr et al. | |
| 2004/0142384 A1 | 7/2004 | Cohen et al. | |
| 2005/0025971 A1 | 2/2005 | Cho et al. | |
| 2006/0141512 A1 | 6/2006 | Sinha et al. | |
| 2008/0044811 A1 | 2/2008 | Haugland | |
| 2008/0206771 A1 | 8/2008 | Liu | |
| 2008/0318250 A1 | 12/2008 | Gilmer et al. | |

(Continued)

FOREIGN PATENT DOCUMENTS

| | | |
|---|---|---|
| EP | 0113452 A2 | 7/1984 |
| EP | 2284256 A2 | 2/2011 |

(Continued)

OTHER PUBLICATIONS

Chan et al. A simple zeta method for sperm selection based on membrane charge. Fertility and Sterility. 85 (2): 481-486 (Feb. 2006).*
International Search Report for PCT/US13/56526 (dated Feb. 7, 2014).
Written Opinion for PCT/US13/56526 (dated Feb. 7, 2014).
Shannon, P. "Contribution of Seminal Plasma, Sperm Numbers and Gas Phase to Dilution Effects of Bovine Spermatozoa." J. Dairy Sci., 48: 1357 (1965).
Shannon, P. et al. "Toxic Effect and Action of Dead Sperm on Diluted Bovine Semen." J. Dairy Sci., 55: 615-620 (1972).

(Continued)

*Primary Examiner* — Gailene Gabel
(74) *Attorney, Agent, or Firm* — Ryan Christensen; Hashim Rahman

(57) ABSTRACT

A method for magnetic cellular manipulation may include contacting a composition with a biological sample to form a mixture. The composition may include a plurality of particles. Each particle in the plurality of particles may include a magnetic substrate. The magnetic substrate may be characterized by a magnetic susceptibility greater than zero. The composition may also include a chargeable silicon-containing compound. The chargeable silicon-containing compound may coat at least a portion of the magnetic substrate. The biological sample may include cells and/or cellular structures. The method may also include applying a magnetic field to the mixture to manipulate the composition.

7 Claims, 10 Drawing Sheets

(56) References Cited

U.S. PATENT DOCUMENTS

| | | | |
|---|---|---|---|
| 2009/0023205 A1 | 1/2009 | Dennig et al. | |
| 2009/0042255 A1 | 2/2009 | Liu | |
| 2009/0101507 A1 | 4/2009 | Aitken et al. | |
| 2009/0208977 A1 | 8/2009 | Hudson et al. | |
| 2009/0306461 A1 | 12/2009 | Oksenberg et al. | |
| 2010/0081130 A1* | 4/2010 | Lee | A61K 49/0002 435/6.16 |
| 2010/0129808 A1 | 5/2010 | Mirkin et al. | |
| 2010/0200405 A1 | 8/2010 | Lenz | |
| 2011/0086336 A1 | 4/2011 | Herickhoff et al. | |
| 2011/0201047 A1 | 8/2011 | Paduch | |
| 2011/0256581 A1 | 10/2011 | Gregory et al. | |
| 2012/0100546 A1 | 4/2012 | Lowery, Jr. et al. | |
| 2012/0270204 A1* | 10/2012 | Fox | B82Y 5/00 435/2 |
| 2018/0045718 A1* | 2/2018 | Krug | C12N 13/00 |

FOREIGN PATENT DOCUMENTS

| | | |
|---|---|---|
| FR | 2811682 A3 | 1/2002 |
| FR | 2827799 A1 | 1/2003 |
| JP | 53056381 A | 5/1978 |
| JP | 601564 A | 1/1985 |
| JP | 2004073112 A | 3/2004 |
| JP | 2012037259 A | 2/2012 |
| JP | 2012037259 A | 6/2012 |
| JP | 2012105579 A | 6/2012 |
| WO | 8806632 A1 | 9/1988 |
| WO | 9007380 A2 | 7/1990 |
| WO | 9741224 A1 | 11/1997 |
| WO | 8806632 A1 | 9/1998 |
| WO | 9958977 A1 | 11/1999 |
| WO | 2004029221 A1 | 4/2004 |
| WO | 2005054808 A2 | 6/2005 |
| WO | 2008095155 A2 | 8/2008 |
| WO | 2010073014 A1 | 7/2010 |

OTHER PUBLICATIONS

Lindemann, C. B. et al. "A Comparative Study of the Effects of Freezing and Frozen Storage on Intact and Demembranated Bull Spermatozoa." Cryobiology, 19: 20-28 (1982).

Saacke, R. G. et al. "Semen Quality Tests and Their Relationship to Fertility." Proc. 4th National Association of Animal Breeders, Tech. Conf. Artificial Insemination and Reproduction, Apr. 18-20, 1972, Madison, WI, National Association of Animal Breeders, Columbia, MO, pp. 22-27.

G.W. Salisbury, G. W. et al. "Physiology of Reproduction and Artificial Insemination of Cattle." second edition, Copyright 1961 & 1978. ISBN 0-7167-0025-5.

Schenk, J. L. et al. "Cryopreservation of Flow-Sorted Bovine Spermatozoa.", Theriogenology 52:1375-1391, 1999.

Parish, J. J. et al. "Capacitation of bovine sperm by Heparin", Biology of Reproduction 38:1171-1180, 1988.

Anzar, M. et al. "Filtration of Bovine Semen. I. Development of a Sephadex Ion-Exchange Filter." Anim. Reprod. Sci. 1993; 31:187-195.

Avery, B. et al. "Impact of Percoll on Bovine Spermatozoa Used for in Vitro Insemination." Theriogenology 1995; 44:871-788.

Correa, J. R. et al. "Preparation and Recovery of Frozen-Thawed Bovine Spermatozoa via Various Sperm Selection Techniques Employed in Assisted Reproductive Technologies." Theriogenology 1996; 46:1225-1232.

Garner, D. L.et al. "Dual DNA Staining Assessment of Bovine Sperm Viability Using SYBR-14 and Propidium Iodide." J Andral 1994; 15:620-629.

Graham, E. F. et al. "The Effect of Whole Ejaculate Filtration on the Morphology and Fertility of Bovine Semen." J. Dairy Sci. 1990; 73:91-97.

Johnson, L. A. et al. "Sex Preselection in Rabbits: Live births from X and Y Bearing Sperm Separated by DNA and Cell Sorting." Biol Reprod 1989; 41:199-203.

Luderer, A. A. et al. "Separation of Bovine Spermatozoa by Density on Water Insoluble Newtonian Gels and Their Use or Insemination." Biol Reprod 1982; 26 (5):813-824.

Pasteur, X. et al. "Identification of Two Human Sperm Populations Using Flow and Image Cytometer." Molecular Reproduction and Development 1994; 38:303-309.

BcMagTm Carboxy-terminated Magnetic Beads. Product Manual. Bioclone, Inc. 2010 http://www.bioclone.us/files/BcMag_Carboxy-Terminated_Magnetic_Beads2.pdf.

BcMagTm Carboxy-terminated Magnetic Beads. Bioclone, Inc. 2010 http://www.bioclone.us/carboxyl-terminated-magnetic-beads-particle-resin-matrix.html.

BcMagTm SAX Magnetic Beads. Bioclone, Inc. 2010. http://www.bioclone.us/Strong-Anion-Exchange-magnetic-beads-particle-resin-matrix.html.

BcMagTm SAX Magnetic Beads. Product Manual. Bioclone, Inc. 2010 http://www.bioclone.us/files/BcMag_SAX_Magnetic_Beads.pdf.

Dynabeads SAX. Invitrogen Dynal Invitrogen Bead Separation; 2007. http://tools.thermofisher.com/content/sfs/manuals/105%2015D_16D_Dynabeads_SAX_rev002.pdf.

Dynabeads WCX. Invitrogen Dynal Invitrogen Bead Separation; 2008. http://tools.thermofisher.com/content/sfs/manuals/105%2011D12D%20%28001%29.pdf.

Dynabeads SCX. Invitrogen Dynal Invitrogen Bead Separation; 2007. http://tools.thermofishercom/content/sfs/manuals/105%2013D_14D%20Dynabeads%20SCX%28rev002%29.pdf.

M-Beads—Magnetic Silica Beads. MoBiTec; Magnetic Silica Beads. 2010.

Qiagen Purification Technologies. QIAGEN anion-exchange, silica gel membrane, and magnetic particle technologies. 2012.

Propidium Iodide Staining Solution Technical Data Sheet. BD Pharmingen. BD Biosciences. 2006.

Dynabeads M-270 Carboxylic Acid. Invitrogen, 2012. https://tools.thermofishercom/content/sfs/manuals/dynabeads_m270carboxylicacid_man.pdf.

Australian Examination Report dated Oct. 27, 2015 for Appl. No. 2013309137.

Said et al. "Utility of Magnetic Cell Separation as a Molecular Sperm Preparation Technique." J Andral. 2008 ; 29(2): 134-142.

Hofmo, Peer Ola "Sperm Sorting and Low-Dose Insemination in the Pig—An Update" Acta Veterinaria Scandinavica 2006, 48(Suppl 1):S11.

Clemente, Henry. "Does Mammalian Sperm have a Charge." ResearchGate. 2013. http://www.researchgate.net/post/Does_mammalian_sperm_have_a_charge.

Peter et al. "Fractionation of Bovine Spermatozoa for. Sex Selection: A Rapid Immunomagnetic Technique to Remove Spermatozoa That Contain the H-Y Antigen." Theriogenology 40:1177-1185, 1993.

Australian Examination Report dated Nov. 6, 2017 in related AU Appl. No. 2016247202.

Canadian Examination Report dated Nov. 20, 2017 in related CA Appl. No. 2883328.

Notice of Allowance dated Aug. 16, 2017 in related U.S. Appl. No. 13/974,139.

Office Action dated Sep. 15, 2015 in related U.S. Appl. No. 13/974,139.

Final Office Action dated Mar. 31, 2016 in related U.S. Appl. No. 13/974,139.

Office Action dated Sep. 8, 2016 in related U.S. Appl. No. 13/974,139.

Final Office Action dated Jan. 1, 2017 in related U.S. Appl. No. 13/974,139.

Office Action dated May 3, 2017 in related U.S. Appl. No. 13/974,139.

Extended European Search Report dated Feb. 19, 2017 in related EP Appl. No. 17208185.3.

Office Action dated Feb. 8, 2017 in related U.S. Appl. No. 14/960,096.

Said et al. "Effects of advanced selection methods on sperm quality and ART outcome: a systematic review." Human Reproduction Update, vol. 17, No. 6, Nov. 2011, pp. 719-733.

European Decision to Grant dated Jan. 25, 2017 in related EP Appl. No. 13832402.5.

(56) References Cited

OTHER PUBLICATIONS

Australian Examination Report dated May 15, 2018 in related AU Appl. No. 2016247202.
U.S. Office Action dated Jun. 8, 2018 in related U.S. Appl. No. 14/960,096.
EP Extended Search Report dated Feb. 17, 2016 for Appl. No. 13832402.5.
Zhaogang "Highly Magnetizable Superparamagnetic Iron Oxide Nanoparticles Embedded Mesoporous Silica Spheres and Their Application for Efficient Recovery of DNA from Agarose Gel" Journal of Materials Chemistry, vol. 19, No. 13, Jan. 1, 2009, p. 1811.
Bruce I J et al: "Synthesis, Characterisation and Application of Silicamagnetite Nanocomposites", Journal of Magnetism and Magnetic Materials, vol. 284, Dec. 1, 2004, pp. 145-160.
CA Examination Report dated Jan. 21, 2016 for Appl. No. 2,883,328.
JP Examination Report dated Feb. 29, 2016 for Appl. No. 2015-529882.
Van Wienen, Marjet et al. "Single Layer Centrifugation with Androcoll-P Can be Scaled-Up to Process Larger Volumes of Boar Semen." ISRN Veterinary Science. vol. 2011, Article ID 548385. pp. 8.
AU Examination Report dated Apr. 8, 2016 for Appl. No. 2013309137.
RU Examination Report dated May 10, 2016 for Appl. No. 2015111211.
AU Examination Report dated Jul. 8, 2016 for Appl. No. 2013309137.
RU Examination Report dated Oct. 4, 2016 for Appl. No. 2015111211.
JP Examination Report dated Oct. 4, 2016 for Appl. No. 2015-529882.
NZ Examination Report dated Nov. 17, 2016 for Appl. No. 705665.
AU Examination Report dated Oct. 27, 2015 for AU Appl. No. 2013309137.
CA Examination Report dated Nov. 25, 2016 for Appl. No. 2,883,328.
EP Examination Report dated Feb. 2, 2017 for Appl. No. 13832402.5.
European Intention to Grant dated Aug. 30, 2017 in related EP Appl. No. 13832402.5.
New Zealand Notice of Acceptance dated Aug. 21, 2017 for NZ Appl. No. 705665.
U.S. Office Action dated Sep. 15, 2015 for U.S. Appl. No. 13/974,139.
U.S. Office Action dated Mar. 31, 2016 for U.S. Appl. No. 13/974,139.
U.S. Office Action dated Sep. 8, 2016 for U.S. Appl. No. 13/974,139.
U.S. Office Action dated Jan. 11, 2017 for U.S. Appl. No. 13/974,139.
U.S. Office Action dated May 3, 2017 for U.S. Appl. No. 13/974,139.
U.S. Notice of Allowance dated Aug. 16, 2017 for U.S. Appl. No. 13/974,139.
Khajavi et al. Can Zeta sperm selection method, recover sperm with higher DNA integrity compare to density gradient centrifugation. Iranian Journal of Reproductive Medicine 7 (2): 73-77 (2009).
U.S. Office Action dated Nov. 4, 2018 in related U.S. Appl. No. 14/960,096.
Indian Examination Report dated Dec. 6, 2018 in related IN Appl. No. 538/KOLNP/2015.
EPO Extended Search Report dated Dec. 12, 2018 in related EP Appl. No. 15866159.5.
New Zealand Examination Report dated Mar. 5, 2019 in related NZ Appl. No.: 734393.
Grunewald et al: "Enrichment of non—apoptotic human spermatozoa after cryopreservation by immunomagnetic cell sorting", Cell and Tissue Banking, 2(3), pp. 127-33. (2001).
Glander et al: "Deterioration of spermatozoal plasma membrane is associated with an increase of sperm lyso-phosphatidylcholines", Andrologia, 34(6), pp. 360-366. (2002).

* cited by examiner

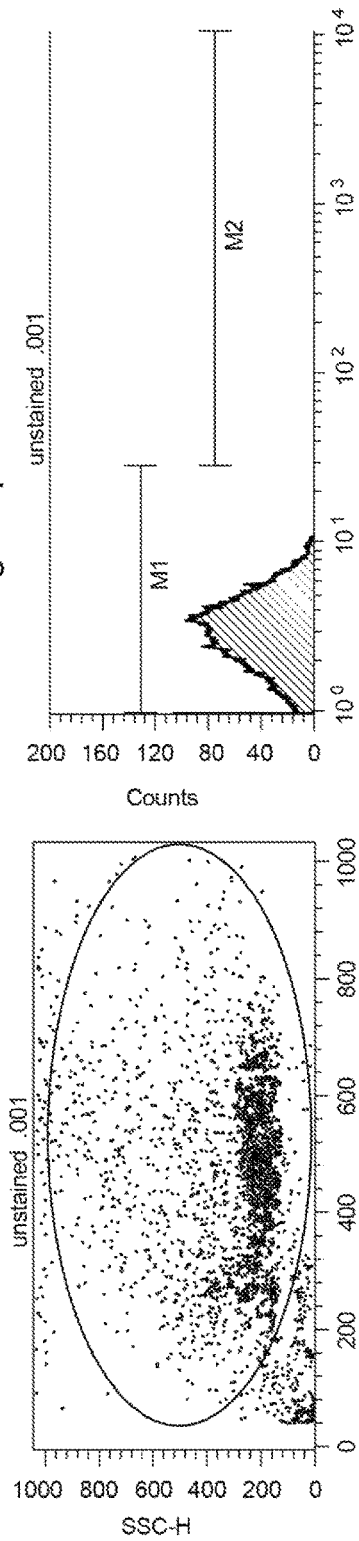
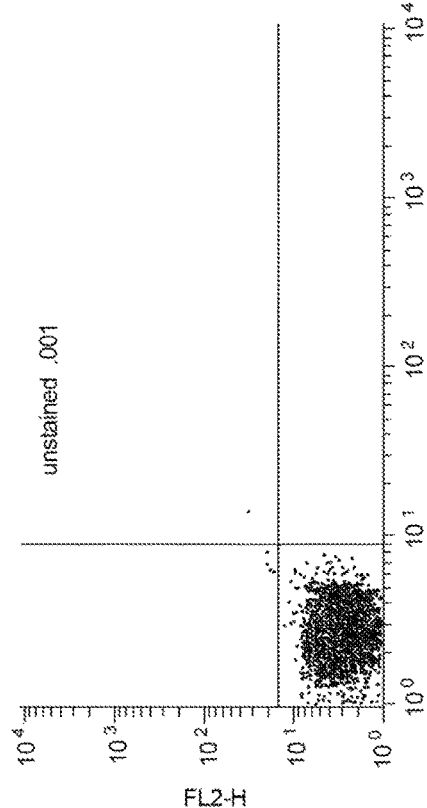
FIG. 1A
FIG. 1B
FIG. 1C

Original percent dead in an untreated sample was 81.32%.

Original live cells would be 18.68%.

Percent Dead in particle treated sample at 34C is 14.73%.
Percent Live cells in Naked treated sample at 34C is 85.27%.

MAGNETIC REMOVAL OR IDENTIFICATION OF DAMAGED OR COMPROMISED CELLS OR CELLULAR STRUCTURES

CROSS-REFERENCE TO RELATED APPLICATIONS

This application is a Continuation of U.S. application No 13/974,139 filed Aug. 23, 2013, now U.S. Pat. No. 9,804,153 issued on Oct. 31, 2017, which claims priority to U.S. Provisional Applications 61/694,756 filed Aug. 29, 2012, the contents of which are all incorporated by reference in their entireties.

BACKGROUND

Increasing the number or percentage of membrane intact, viable cells in a sample may improve overall sample quality, and may increase the success of subsequent procedures. For example, an increase in the number or percentage of membrane intact, viable sperm in a fresh or frozen/thawed sample may improve overall sperm quality. Cleavage rates for both in vitro and in vivo fertilization procedures may be increased. Embryo quality may be enhanced and embryonic losses may be reduced, which may lead to increased pregnancy rates.

Magnetic cellular separation of apoptotic sperm has been achieved using annexin V. However, it is desirable to remove sperm cells and sperm cellular structures compromised in ways other than just apoptosis. Moreover, annexin V technology may be limited because the binding buffer may negatively affect sperm motility. Further, the cost of the reagents may potentially limit routine clinical application and adaptation of the protocol to handle higher volumes and cell concentrations.

The present application appreciates that magnetic cellular manipulation may be a challenging endeavor.

SUMMARY

In one embodiment, a composition for magnetic cellular manipulation is provided. The composition may include a plurality of particles. Each particle in the plurality of particles may include a magnetic substrate. The magnetic substrate may be characterized by a magnetic susceptibility greater than zero. Each particle in the plurality of particles may also include a chargeable silicon-containing compound. The chargeable silicon-containing compound may coat at least a portion of the magnetic substrate.

In another embodiment, a method for magnetic cellular manipulation is provided. The method may include contacting a composition with a biological sample to form a mixture. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate. The biological sample may include cells and/or cellular structures. The method may also include applying a magnetic field to the mixture to manipulate the composition.

In one embodiment, a kit for magnetic cellular manipulation is provided. The kit may include instructions. The instructions may include contacting a composition with a biological sample to form a mixture. The instructions may also include applying a magnetic field to the mixture to manipulate the composition. The kit may also include the composition. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate.

Additional objects, advantages, and novel features of the described methods and processes will be set forth, in part, in the description that follows; and, in part, will become apparent to those skilled in the art upon examination of the following; or may be learned by practice of the described methods and processes. The objects and advantages of the described methods and processes may be realized and attained by means of the instrumentalities and combinations particularly pointed out, as well as those items shown by inference.

BRIEF DESCRIPTION OF THE DRAWINGS

The accompanying figures, which are incorporated in and form a part of the specification, illustrate one or more embodiments of the described methods and processes as related to sperm cells, and, together with the description, serve to explain the broad general cellular principles of the described methods and processes.

FIG. 1A shows flow cytometry analysis of an unlabeled ejaculate sample before example magnetic particle treatment, plotted as side light scatter (SSC-H) as a function of forward light scatter (FSC-H) measurements;

FIG. 1B shows flow cytometry analysis of an unlabeled ejaculate sample before example magnetic particle treatment, plotted as fluorescence height (FL2-H) in counts, with nearly all cells live (M1);

FIG. 1C shows flow cytometry analysis of an unlabeled ejaculate sample before example magnetic particle treatment, plotted as a two-parameter dot plot of two fluorescence height measurements, FL2-H and FL1-H;

DETAILED DESCRIPTION

Figure 1E:
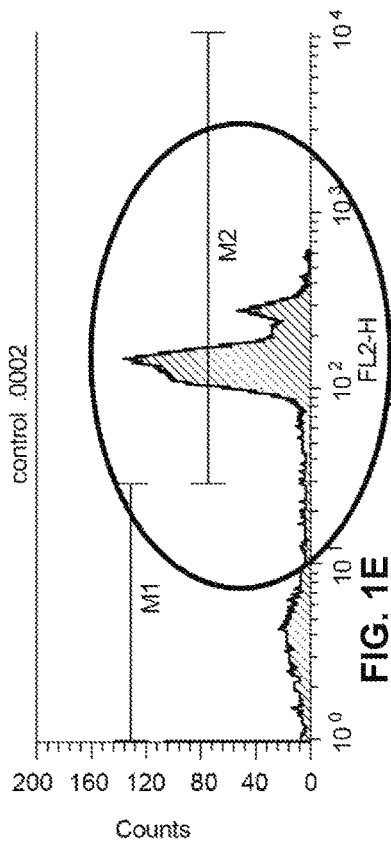
FIG. 1E shows flow cytometry analysis of an ejaculate sample before example magnetic particle treatment, labeled with propidium iodide, plotted as fluorescence height (FL2-H) in counts, showing original dead untreated cells (M2, 81.32%) and original live cells (M1, 18.68%)

The described methods and processes may include a variety of aspects, which may be combined in different ways and may be applied to differing cells or cellular materials. The following descriptions are provided to list elements and describe some of the embodiments of the described methods and processes. These elements are listed with initial embodiments and are shown in examples of an embodiment relative to sperm as but one initial example. However, it should be understood that each and every permutation and combination of all aspects disclosed may be applied in any manner and in any number to create additional embodiments for additional cells or cellular structures. The variously described examples and preferred embodiments should not be construed to limit the described methods and processes to only the explicitly described systems, techniques, and applications. Further, this description should be understood to support and encompass descriptions and claims of all of the various embodiments, systems, substances, elements, techniques, methods, devices, and applications with any number of the disclosed elements, with each element alone, and also with any and all various permutations and combinations of all elements in this or any subsequent application.

Briefly described, embodiments of the described methods and processes include a method for removing or identifying cells or cellular structures having damaged membranes from those with intact membranes, thereby enriching sample or cellular viability. The method may be applied to cells such as contained in freshly collected samples, after dilution, during and after cooling, or during and after other cell or system procedures that may be employed prior to cryopreservation, or to frozen/thawed cell samples. The method may also be used for samples that may be used immediately. The method may also be used for samples that may be held for a period of time or extended in buffers or other substances. For example, the method may also be used for samples that may be held at 4° C. to 40° C. for at least about 12, 24, 30, 36, 48, 60, 72 hours or more. The method may also be used for samples that include but are not limited to samples that have an osmolarity of 250-375 mOsm. The enriched cell populations may be used for routine procedures, prior to or after other processing techniques, prior to or after shipment of samples, and prior to or after long-term cryopreservation or other processes.

Embodiments related to sperm may include a method for removing sperm having damaged membranes from those with intact membranes to enrich sperm viability of a sperm sample. The method may be applied to sperm contained in freshly collected neat ejaculates, after dilution, during and after cooling, or during and after other semen processing procedures that may be employed prior to cryopreservation, or to frozen/thawed sperm. The method may also be used for neat or extended sperm samples to be used immediately. The method may also be used for neat or extended sperm samples held up to 30 h at 4° C. to 40° C., or extended in sperm rich buffers that have an osmolarity of 250-375 mOsm. The enriched sperm populations may be used for routine artificial insemination, prior to or after sperm sexing techniques, prior to or after shipment of semen for routine or sperm sexing purposes or cryopreservation purposes, or for in vitro fertilization, for all mammalian sperm.

In some embodiments, damage to the membranes of intact cells may be reduced by removing known harmful effects caused by damaged cells. For example, DNA fragmentation, oxidative damage caused by peroxidation, and the premature release of proteolytic and hydrolytic enzymes may be examples of effects attributable to membrane damage. Damage to cell sample integrity may reduce lifespan both in vitro and in vivo, may reduce desired cellular functional ability, and may cause poor resultant capabilities.

With respect to sperm as one, non-limiting example, damage to the membranes of intact sperm may be reduced by removing known harmful effects caused by damaged sperm. For example, DNA fragmentation, oxidative damage caused by peroxidation, and the premature release of proteolytic and hydrolytic enzymes may be examples of sperm damage caused by membrane damaged sperm. Damage to spermatozoal integrity may reduce sperm lifespan both in vitro and in vivo, may reduce fertilization ability, and likely causes poor embryo quality, which may be a major source of infertility in mammals.

Mammalian sperm with good fertility may exhibit a high frequency of morphologically-normal, viable sperm. Current procedures for semen processing for sex selection, cooling, or cryopreservation may have detrimental effects on the metabolism and motility of sperm, as well as on the status of sperm membrane domains. The net result of these effects may be reduced sperm functionality. Magnetic removal of damaged or compromised cells or cellular structures may reduce a detrimental effect on the quality of live and normal sperm that may be caused by dead and abnormal sperm.

The pH of the medium suspending the cells may affect the charge of proteins comprising the cells. Proteins may function as dipolar ions, for example, due to the ionization of the various R groups of the amino acids that make up their primary structure. Medium pH may affect interactions between such proteins. For example, capacitation of sperm may involve removal of seminal coating proteins absorbed on the sperm's surface membrane. Increasing the pH of the capacitating medium from may be expected to alter the binding of proteins to the sperm's surface. Altering the binding of proteins to the sperm's surface may cause or be associated with capacitation. For example, the capacitating medium may have a baseline pH between about 6.5 and 8.5, or in some examples between about 7.2 and about 8.4. The capacitating medium may increase in pH in association with or in causation of successful capacitation. The increase in pH of the capacitating medium in association with or in causation of successful capacitation may be, in pH units, at least about 0.1, 0.15, 0.2, 0.25, 0.3, 0.35, 0.4, 0.45, 0.5, 0.6, 0.7, 0.8, 0.9, or 1. In some examples, the increase in pH in association with or in causation of successful capacitation may be about 0.36 pH units.

Ionic components of the culture medium may influence mammalian sperm motility and a sperm's ability to penetrate an oocyte. The pH of the medium may cause the ionization of substances within the medium, for example, including intrinsic sperm membrane proteins and extrinsic, absorbed seminal plasma proteins. The pH of the medium may determine many aspects of the structure and function of biological macromolecules, including enzyme activity, and the behavior of cells.

The net charge on a cell surface may be affected by pH of the surrounding environment and may become more positively or negatively charged due to the loss or gain of protons. At or near physiological sperm pH, the net surface charge may be negative. Biological membranes, including sperm, may be negatively charged in physiological pH, mainly as a result of the presence of acidic phospholipids. About 10-20% of the total membrane lipids may be anionic. Because the membrane may be exposed to surrounding aqueous buffer, specific interactions with outer medium components may occur. Charged groups of membrane components and solutions ions may be involved in the resulting equilibria. The equilibria may be affected by different factors and processes leading to a membrane surface charge density variation. The net charge may be also influenced by membrane composition, ionic strength of electrolytes, and solution pH.

Viable mammalian sperm may have a net negative surface charge at the plasma membrane. As sperm undergo capacitation followed by the acrosome reaction, net charge may become less negative and more positive. The net charge may become less negative and more positive due to, for example, loss of negative groups, such as sialic acid groups. Capacitation may be characterized by the removal of coating materials from the sperm surface. Capacitation may be the penultimate step in fertilization, resulting in an increased permeability of the plasma membrane to $Ca^{2+}$ ions, and allowing the sperm to undergo the acrosome reaction or death if fertilization does not occur. A viable mature human sperm may have a negative zeta potential of −16 to −20 mV (differential potential between the sperm membrane and its surroundings), which may decrease with capacitation to become more positively charged or near zero.

Sperm pre-capacitation may result in ova fertilization failure. Further, damage to sperm chromatin may result in poor embryo quality. Because fertilization, as one example of many other cellular functions in this class, may be a time-sensitive event and good embryo quality may be essential for timely embryo development, both may be adversely affected by sperm quality. Factors released from damaged sperm or other cells may be partly responsible for further cellular damage to the remaining subpopulation of cells such as normal sperm. For example, freshly killed dead sperm may have reduced livability of sperm in diluted bovine semen. Further, freshly ejaculated sperm subjected to elevated temperatures before ejaculation may exhibit high reactive oxidative species levels. Thus, the toxic effect of dead cells, including but not limited to sperm, may be due to amino acid oxidase activity. Dead and abnormal cells such as sperm may have toxic effects on companion cells. Dead and abnormal cells may reduce cellular sample functionality such as fertility.

In various embodiments of the described methods and processes, carboxyl group functionalized, silane-coated magnetic particles may be used ranging in physical diameter from 300 nm to 800 nm and an average hydrodynamic diameter of about 330 nm. In some embodiments, the carboxyl group functional silane coated magnetic particles may be used without further surface manipulation since the carboxyl group on the silane contributes to the particles having a net negative electrical charge or zeta potential. Sperm may increase in intracellular pH with capacitation, which may cause the membrane of the capacitated and dead sperm to lose net negative zeta potential and shift toward a neutral (zero) or more positive zeta potential. The negatively charged magnetic particles may bind specifically to compromised, damaged, or dead sperm. In addition, the silane surface may also be conjugated to other substances such as by standard EDC/NHS chemistry. In some examples, EDC-mediated coupling efficiency may be increased by adding the presence of substances such as amine reactive esters for the conversion of carboxyl groups to amines.

In various embodiments, the described processes and methods may be used to differentiate necrotic, apoptotic, and normal cells. In the example discussed, the carboxyl modified silane surface binds to the membrane of the dead and dying sperm through an electrical charge interaction known as zeta potential. Material may spontaneously acquire a positive or negative surface electrical charge when brought into contact with a polar medium (e.g., water). For example, an interface in deionized water may be negatively charged. An ionization of surface groups to form a surface electrical charge may be observed with metal oxide surfaces (M-OH) as well as materials that may contain carboxyl and/or amino groups, such as proteins, ionic polymers, and polyelectrolytes. Ionization and/or dissociation, degree of charge development, net molecular charge, and sign, either positive or negative, may depend on the pH of the surrounding medium.

The conjugation of carboxyl group functional magnetic particles may additionally be applied to, for example, fluorescent stains. SYBR-14 and bis-benzamide are example membrane permeable stains that may be used to distinguish cells from other background substances. In the sperm cell embodiment, such fluorescent stains may distinguish sperm cells from diluent particles frequently found in extenders employed in non-frozen storage or cryopreservation of sperm. Other examples of fluorescent probes may include JC-1 and rhodamine 123, which may be used to assess the respiration rate of cell mitochondria; or fluorescently labeled agglutinins from the pea (PSA) or peanut (PNA) that may be used to detect acrosome-reacted cells such as sperm. Other labels include but are not limited to acridine orange (e.g., to remove apoptotic cells); 7-aminoactinomycin D (7-AAD), which may be also a DNA intercalating agent in double stranded DNA with a high affinity for GC rich regions; food coloring such as Allura Red (FD&C Red #40), Sunset Yellow (FD&C Yellow #6), Indigo carmine (FD&C Blue #2), and Fast Green FCF (FD&C #3).

The cell plasma membrane may cover the entire cell and may have distinct membrane compartments, such as, in the sperm cell example, the head, middle and principal portions. Since the plasma membrane may be composed of distinct membrane compartments, different stains may be used alone or in combination with other stains to assess the integrity of the different plasma membrane compartments.

In some embodiments of the described methods and processes, cells with varying degrees of membrane damage may be labeled with magnetic particles containing a charged surface. This may be in contrast to the use of annexin-V/microbead magnetic cell sorting procedures that fail to identify and/or remove pre-capacitated or acrosomal reacted sperm because the PS does not become externalized in these examples. When membrane damaged sperm or cellular structures labeled with the surface charged magnetic particles are placed in a magnetic field, such cells or cellular structures may be eliminated from the general population. The resultant harvested sub-population of viable cells, perhaps such as sperm, may be further processed for cryopreservation, non-frozen transport and storage, functional utilization (such as sex selection for sperm), or used in related aspects, perhaps such as assisted reproductive technologies (ARTs) for sperm or the like.

Embodiments of the described methods and processes may be used with any type of magnetically identifying separating apparatus, including but not limited to devices incorporating columns, such as magnetic-activated cell sorting (MACS) products, devices using simple magnetic fields applied to test tubes or containers, or high throughput magnetic devices.

Targeted dead and dying cells labeled with magnetic particles and subjected to magnetic cell separation in an open, column-less magnetic system may be removed more efficiently and in greater numbers per time unit compared to flow cytometry. Magnetic cell separation may be utilized with no internal operating pressure, or if pressurized, a lower internal operating pressure; and the stream of fluid containing the cells may avoid being broken into cell damaging droplets as for flow cytometry. Further, the sheath fluid for flow cytometry may be generally a salt-based, lipoprotein-deficient physiological medium. Magnetic cell separation may allow some cells, such as sperm, to be bathed in nutrient-rich buffers that may promote and prolong cell viability during the separation procedure.

The described methods and processes may remove necrotic cells or cellular structures that have been traumatized during cell processing procedures such as cryopreservation, centrifugation, and staining. Necrotic damage may occur by different cellular processes than that caused in one example by sperm senescence, which may be a naturally occurring cause of cellular death.

In other magnetic cell separation applications, embodiments of the described methods and processes may be used to label cells uniquely, such as sperm, with one or more fluorochrome stains, targeting a specific cell or sperm attribute. The targeted cell or sperm cell may be selectively killed or rendered non-functional, with an energy source, including but not limited to an electrical charge or pulse of laser light. The described methods and processes may be used to magnetically label and ultimately remove the non-functional cell or sperm through magnetic cell separation procedures. The resultant desired sub-population of harvested cells may be selected for membrane intactness (viability) as well as for specific cellular attributes, including but not limited to, in the sperm example, chromosomal sex selection.

In various embodiments, a composition for magnetic cellular manipulation is provided. The composition may include a plurality of particles. Each particle in the plurality of particles may include a magnetic substrate. The magnetic substrate may be characterized by a magnetic susceptibility greater than zero. Each particle in the plurality of particles may also include a chargeable silicon-containing compound. The chargeable silicon-containing compound may coat at least a portion of the magnetic substrate.

"Magnetic susceptibility" means the response of a sample, such as the magnetic substrate, to an externally applied magnetic field. For example, a magnetic susceptibility of less than or equal to zero may be associated with diamagnetism. A magnetic susceptibility of greater than zero may be associated with magnetic properties other than diamagnetism. For example, in various embodiments, the magnetic substrate may be characterized by one or more of paramagnetism, superparamagnetism, ferromagnetism, or ferrimagnetism. The magnetic substrate may include a metal oxide, such as a transition metal oxide, for example, an iron oxide. In some examples, the magnetic substrate may include $Fe_3O_4$.

A "chargeable silicon-containing compound" is any silicon containing molecule, polymer, or material that may be caused to acquire or hold a charge, e.g., via functionalization with charged or chargeable moieties. Chargeable/charged moieties may include, but are not limited to, species (and ions thereof) of: metals; oxides; carboxylates; amines; amides; carbamides; sulfates; sulfonates; sulfites; phosphonates; phosphates; halides; hydroxides; and combinations thereof. For example, the chargeable silicon-containing compound may include 2-(carbomethoxy)ethyltrimethoxysilane.

In various examples, the composition may include a zeta potential charge. For example, the chargeable silicon-containing compound may include a negative zeta potential charge. The chargeable silicon-containing compound may include a positive zeta potential charge. In some examples, at least a portion of the plurality of particles may include a first zeta potential charge. The portion of the plurality of particles may form a complex with one or more cells or cellular structures that include a second zeta potential charge. The second zeta charge may be opposite in sign compared to the first zeta charge. In several embodiments, at least a portion of the plurality of particles may include a negative zeta potential charge. The portion of the plurality of particles may form a complex with one or more sperm cells or sperm cellular structures that include a positive zeta potential charge.

In various embodiments, the plurality of particles may include at least one of a protein, an antibody, and a dye. The protein, antibody, or dye may be conjugated to the chargeable silicon-containing compound. For example, the chargeable silicon-containing compound may include 2-(carbomethoxy)ethyltrimethoxysilane, and the protein, antibody, or dye may be conjugated to the 2-(carbomethoxy) group, e.g., via an amide bond.

In another embodiment, a method for magnetic cellular manipulation is provided. The method may include contacting a composition with a biological sample to form a mixture. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate. The biological sample may include cells and/or cellular structures. The method may also include applying a magnetic field to the mixture to manipulate the composition.

A "biological sample" may include any natural or prepared composition that includes the cells and/or cellular structures. Natural samples may include, for example, biological fluids containing cells or cellular structures, such as blood, lymphatic fluids, intestinal fluids, intercellular fluids, sweat, tears, urine, semen, mucosal secretions, synovial fluid, and the like. Natural samples may include fluids typically free of cells or cellular structures, but which may include cells or cellular structures as part of injury, illness, genetic defect, or other pathological conditions. Prepared samples may include any biopsy, tissue homogenate, or other prepared form of biological tissue. Typically, the biological sample will include at least one cell or cellular structure characterized by a zeta potential charge. The biological sample may include at least two or more cells or cellular structures characterized by zeta potential charges differing in sign or charge density. For example, a biological sample may include a first cell characterized by a first zeta potential charge and a second cell characterized by a second zeta potential charge opposite in sign to the first zeta potential charge.

In some embodiments, the method may include causing the chargeable silicon-containing compound to acquire a first zeta potential charge. The first zeta potential charge may be opposite in sign compared to a second zeta potential charge comprised by the cells and/or cellular structures in the biological sample. Causing the chargeable silicon-containing compound to acquire the first zeta potential charge may include contacting the chargeable silicon-containing compound to a polar medium, as described herein.

In several embodiments, the method may include causing the composition and at least a portion of the cells and/or cellular structures in the biological sample to form a complex. Applying the magnetic field to the mixture to manipulate the composition may manipulate the complex.

In some embodiments, at least a portion of the plurality of particles further comprises at least one of a protein, an antibody, and a dye.

In several embodiments, the biological sample may include viable cells and damaged or compromised cells or cellular structures. The composition may selectively form a complex with one of the viable cells or the damaged or compromised cells or cellular structures, for example according to a first zeta potential charge on the composition and an opposite second zeta potential charge on one of the viable cells or the damaged or compromised cells or cellular structures. The method may further include separating the viable cells from the damaged or compromised cells or cellular structures by applying the magnetic field to the mixture. Because the composition may selectively form a complex with one of the viable cells or the damaged or compromised cells or cellular structures, the portion of the biological sample forming the complex with the composition may be magnetically manipulated and separated from portions of the biological sample not forming the complex with the composition. The method may therefore be a method for selectively and magnetically separating portions of the biological sample according to zeta potential charge.

In various embodiments, the biological sample may include viable sperm cells and damaged or compromised sperm cells or sperm cellular structures. The composition may form a complex with the damaged or compromised sperm cells or sperm cellular structures. The method may further include separating the viable sperm cells from the complex including the damaged or compromised sperm cells or sperm cellular structures by applying the magnetic field to the mixture. Because the composition may selectively form a complex with the damaged or compromised sperm cells or sperm cellular structures, the complex with the damaged or compromised sperm cells or sperm cellular structures may be magnetically manipulated and separated from the viable sperm cells. The method may therefore be a method for selectively and magnetically separating viable sperm cells from the damaged or compromised sperm cells or sperm cellular structures according to zeta potential charge.

In several embodiments, the method may include subjecting the sperm sample to detection, for example fluorescence detection as described herein.

In various embodiments, a kit for magnetic cellular manipulation is provided. The kit may include instructions. The instructions may include contacting a composition with a biological sample to form a mixture. The instructions may also include applying a magnetic field to the mixture to manipulate the composition. The kit may also include the composition. The composition may include a plurality of particles. Each particle in the plurality of particles may include a magnetic substrate. The magnetic substrate may be characterized by a magnetic susceptibility greater than zero. Each particle in the plurality of particles may include a chargeable silicon-containing compound. The chargeable silicon-containing compound may coat at least a portion of the magnetic substrate.

In some embodiments of the kit, the biological sample may include viable cells and damaged or compromised cells or cellular structures. The composition may form a complex with one of the viable cells or the damaged or compromised cells or cellular structures. The instructions may further include separating the viable cells from the damaged or compromised cells or cellular structures by applying the magnetic field to the mixture.

In several embodiments of the kit, the composition may be configured for forming a complex with damaged or compromised sperm cells or sperm cellular structures. The instructions may further include selecting the biological sample comprising viable sperm cells and damaged or compromised sperm cells or sperm cellular structures. The instructions may also include separating the viable sperm cells from the complex including the damaged or compromised sperm cells or sperm cellular structures by applying the magnetic field to the mixture.

Having generally described the present method, more details thereof may be presented in the following EXAMPLES. Although the examples involve sperm cells as the cell item, the selection or application is not intended to limit the scope of the described methods and processes, as other types of cells are valuable in applications of the general teaching of the described methods and processes.

EXAMPLE 1

Particle Preparation for Magnetic Staining of Dead/Damaged Cells with Sperm as a Representative, Non-Limiting Example Magnetic cores: Magnetic cores may be fabricated such as by co-precipitation of $Fe_3O_4$ with $Fe_2O_3$ so that the magnetic susceptibility of the particles in a chosen magnetic field may be sufficiently high to provide rapid separation of magnetically labeled cells from non-labeled cells. The core may be comprised of any magnetic material; possible non-limiting examples include: (1) ferrites such as magnetite, zinc ferrite, or manganese ferrite; (2) metals such as iron, nickel, or cobalt; and (3) chromium dioxide. In one embodiment, the iron cores are comprised of magnetite ($Fe_3O_4$). In other embodiments the core may be extended to include substances such as other iron oxide based nanoparticle materials including composites having the general structure $MFe_2O_4$ (where M may be Co, Ni, Cu, Zn, Mn, Cr, Ti, Ba, Mg, or Pt).

Thus, in this one non-limiting example, a reaction chamber containing 400 mL of $dH_2O$ in a water kettle was warmed to 60° C. To the 400 mL of warmed $dH_2O$, 23.4 g of $FeCl_3.6H_2O$ and 8.6 g of $FeCl_2$ or the like was added and the mixture was stirred under $N_2$ gas. To this solution, 30 mL of 25% $NH_3.H_2O$ was added and mixing was continued under $N_2$ gas. Almost immediately, the orange salt mixture turned to a dark brown/black solution. The heat was turned off and the ferrofluid slurry was allowed to cool while being vigorously stirred for 30 min. The precipitate was collected magnetically and the supernatant was decanted. To the magnetically collected ferrofluid, 800 mL of $dH_2O$ was added, swirled, and the magnetic collected process was repeated. The washing process was repeated four times to remove substantially all residual $NH_3.H_2O$ and any non-magnetic particles. The final wash step may include a solution of 800 mL 0.02 M NaCl in $dH_2O$ or the like. The collected iron core sizes were between approximately 3 and approximately 10 nm.

Coating of Iron Cores with a functionalizable surface: The final outer layer may comprise a polymer coat that interacts with the aqueous environment and serves as an attachment site for proteins and ligands. Suitable polymers may include polysaccharides, alkylsilanes, biodegradable polymers such as, for example, poly(lactic acids) (PLA), polycaprolactone (PCL), and polyhydroxybutyrate-valerate (PHBV); composites, and polyolefins such as polyethylene in its different variants. More specifically, polysaccharide chains may include dextrans, arabinogalactan, pullulan, cellulose, cellobios, inulin, chitosan, alginates, and hyaluronic acid. Silicon containing compounds such as alkylsilanes may also be employed to encapsulate the magnetic core. Alkylsilanes suitable for embodiments of the described methods and processes, may include but are not limited to, n-octyltriethoxysilane, tetradecyltrimethoxysilane, hexadecyltriethoxysilane, hexadecyltrimethoxysilane, hexadecyltriacetoxysilane, methylhexadecyldiacetoxysilane, methyl-hexadecyldimethoxysilane, octadecyltrimethoxysilane, octadecyltrichlorosilane, octadecyltriethoxysilane, and 1,12-bis(trimethoxysilyl)dodecane. In one example, the ratio of iron to silicon containing compound coating may be approximately 0.2. In other embodiments, the ratio of iron to silicon containing compound coating may be greater than about 0.2, such as about 0.4 or 0.8, with a view toward completely coating the iron cores such that the iron cores may be removed from the cell suspension within the magnetic field. Undercoated particles may result in the free metal oxide crystals which may be detrimental to cell viability. In still other embodiments, the ratio of iron to silicon containing compound coating may be less than 0.2. Indeed, the iron concentration divided by the silicon containing compound concentration may be from about 0.1 to about 1.

For the examples of magnetic removal of dead/dying or compromised cells such as sperm, a silicon containing compound may be used to encapsulate the iron cores.

The iron core precipitate may be allowed to settle. With the understanding that throughout this disclosure all amounts, times, and values may be varied up or down such as by 10%, 20%, 30%, or even 40% in any permutation or combination for some embodiments, 67.1 mg of the ferrofluid were added to 100 mL of 10% 2-(carbomethoxy) ethyltrimethoxysilane. 2-(carbomethoxy)ethyltrimethoxysilane is yet another example of a silicon containing compound that is suitable for use in the described methods and processes as a silicon containing compound coating. The pH was adjusted to 4.5 using >99.5% glacial acetic acid, and the suspension was reacted at 70° C. for 2 h under $N_2$ gas with vigorous mixing. After cooling, the particles may be magnetically collected and washed with $dH_2O$. After washing, the silane-coated magnetic nanoparticles may be suspended in 5 mL of 0.05 M 2-(N-morpholino)ethanesulfonic acid (MES) Buffer, TRIS Buffer, TALP buffer, or it may remain in the $dH_2O$ until use for separation. The resuspension buffer may be at a pH that retains or creates a net negative zeta potential of the particles.

Iron concentration may be determined using Inductively Couple Plasma-Optical Electron Spectroscopy (ICP-OES), and the iron concentration may be adjusted according to milligrams per milliliter needed for optimal dead cell removal. The particles may have an average hydrodynamic diameter of 300 nm, and need to be in a range of 300 to 1000 nm to stay suspended in solution so that maximum interaction between the cells and particles is achieved by keeping the particles in suspension and not settling out due to larger sizes.

Coupling of proteins and ligands to the particle surfaces: In the event that the surface of the particles needs to be treated and conjugated to a protein or antibody, the following methods may be used. Periodate treatment of dextran and other polymers are one method for the attachment of proteins due largely to the large number of reactive groups that are available for modification. Mild sodium periodate treatment may create reactive aldehyde groups by oxidation of adjacent hydroxyl groups or diols. Proteins, antibodies, streptavidin, and amino-modified nucleic acids may be added at high pH to allow amines to form Schiff bases with the aldehydes. The linkages may be subsequently reduced to stable secondary amine linkages by treatment with sodium borohydride or sodium cyanoborohydride, which may reduce unreacted aldehyde groups to alcohols. Another method of coupling proteins to the magnetic nanoparticles may be to create stable hydrazine linkages. For example, a protein may be coupled to dextran using succinimidyl 4-hydrazinonicotinate acetone hydrazone (SANH; Solulink Inc, San Diego, Calif.). The reaction may use five-fold less protein, and the resulting protein density may appear as high as with other methods. The SANH reagent may allow more efficient and gentle coupling of ligands to the dextran surface. Ligand attachment on silica-coated magnetic nanoparticles may be completed using (3-aminopropyl)triethoxysilane (APTS) to introduce amines on the particle surface while (3-mercaptopropyl)triethoxysilane (MPTMS) introduces SH groups. The heterobifunctional coupling agent (Succinimidyl 4-[N-maleimidomethyl]cyclohexane-1-carboxylate) may then be used to link thiols to the amines. As examples, amines on the particle surface may be linked to thiols on streptavidin molecules, and thiols on the particle surface may be linked to amines on streptavidin. There are several methods of crosslinking proteins through chemical modifications known in the art that may be used for the present embodiments of the described methods and processes. For this example, the carboxylic acid functionalized silane may attach proteins and ligands through EDC chemistry.

EDC Activation of COOH groups on Particle Surface Activation: The silanized particles were re-suspended in 0.05 M MES buffer, collected magnetically, and the supernatant may be aspirated and discarded. Another 5 mL of MES buffer (0.05 M, pH 4.7-5.2) per 10 mg of iron was added to the particles and the suspension was vigorously shaken. Particles were magnetically collected, and the supernatant was aspirated and discarded. This step may be repeated two or so additional times. Frozen EDC was allowed to thaw at room temperature for 30 min. EDC (also known as EDAC or EDCI, 1-ethyl-3-(3-dimethylaminopropyl) carbodiimide), commonly obtained as a hydrochloride, is a water soluble carbodiimide, which is typically employed at pH in the range between 4.0 and 6.0. EDC may be used as a chemical crosslinker for collagen, reacting with the carboxylic acid groups of the collagen polymer which may then bond to the amino group in the reaction mixture.

1.6 mg of EDC/mg iron was added to the particle suspension and the suspension was shaken vigorously. Each tube or the like containing particles and EDC was be placed on a laboratory rocker at room temperature for 30 min. After 30 min., particles were magnetically collected, and the supernatant was aspirated and discarded. Buffers of varying salt concentrations, molarities, including but not limited to, 0.1 M to 1 M, and pH ranges from 10 to 4.7 may be used for protein conjugation to the various surfaces. The function of each antibody, protein and ligand optimizes at different pH ranges and molarities, as is known in the art (Hermanson, Bioconjugate Techniques, 2008). In this example, the particle pellet was added to 0.05M MES buffer, particles may be magnetically collected, and supernatant may be aspirated and discarded. This step may be repeated three or so times. 10 mg of protein, ligand or stain was suspended in 0.05M MES buffer and added to the particles so that the total labeling volume was about 5 mL per 10 mg of iron.

A stoichiometric balance of 1 mg of protein, ligand, or stain per 1 mg of iron was used for the coupling reaction. Some experiments suggested that the best binding of dead or compromised cells is concentration dependent and may occur at about this concentration (with the above percentage variations applicable, of course). The range in antibody or protein used may include, but is not limited to, 0.125 mg to 5 mg of antibody per mg of iron. Tubes were shaken and placed on a laboratory rocker at room temperature for 24 h, and particles were magnetically collected. The supernatant was aspirated and discarded. Each particle suspension was suspended in 5 mL of MES buffer. To each tube, 5 mL of quenching solution (1M glycine, pH 8.0) was added and the tubes were shaken vigorously. Quenching solutions may include, but are not limited to, 2-mercaptoethanol, ethanolamine, glycine, UV exposure, size exclusion and magnetic collection. Each tube was placed on a laboratory rocker for 30 min. at room temperature. After 30 minutes, 5 mL of wash buffer was added to each tube and shaken to mix. The particles were magnetically separated, and the supernatant was aspirated and discarded. This step may be repeated 4 or so times. After the conjugation process was complete, particles were magnetically collected, washed, and filtered to obtain a size distribution of 50 to 400 nm. After the wash steps, each particle suspension was suspended in a buffer for the particular cells, such as for sperm cells or other such cells, with a pH (6.0-8.0) and osmolarity (250-350) suitable for optimal sperm or other cell viability such as but not limited to TRIS solution, Sodium Citrate solution, TEST solution, egg yolk-TRIS (pH 6.5-7.4), egg yolk-sodium citrate (pH 6.5-7.4), egg yolk-TEST (pH 6.5-7.6), milk extenders (pH 6.5-7.4), commercially available extenders marketed by IMV International, Maple Grove, Minn., USA and MiniTube GmbH, Vernona, Wis., USA and chemically defied media including but limited to TALP (pH 6.0-8.0) Tyrodes (pH 6.0-8.0) and Hepes BGM-3 (pH 6.0-8.0) so that the resultant working iron concentration was about 4 mg/mL as confirmed by Inductive Coupled Plasma-Optical Emission Spectroscopy (ICP-OES).

The particles may be advantageously on the order of about 300 nm so that interaction between the particles and that of the damaged or dead cells is maximized in solution. If particles are too large, such interaction may not occur due to the settling effect of the larger sized particles in solution. If particles are smaller than approximately 30 nm, they may either not be sufficiently magnetic and higher magnetic susceptibility core materials within a chosen magnetic energy field will have to be generated, or these small particles may contribute to nonspecific binding; that is, they may bind to viable cells as well as to dead and dying cells. If nonspecific binding relating to particle size is problematic, particle size may either be increased, or a blocking agent dependent upon the particular cells involved, such as nonfat dried milk or serum albumin for sperm, may be added to the labeling buffer solution to minimize such nonspecific binding.

The surface charged particles used in Examples 2-4 are comprised of $Fe_3O_4$ coated with 2-(carbomethoxy)ethyltrimethoxysilane, without further activation or functionalization. The ratio of iron to silicon containing compound coating is approximately 0.2.

EXAMPLE 2

Removal of Damaged Cells

Removal of dead and dying sperm from a thawed cryopreserved semen sample. Six straws of semen were obtained from liquid nitrogen and thawed in a water batch for 2 min.

Contents of all six straws were emptied into one 50 mL falcon tube (about 240 million sperm). About 10 mL of bovine sheath fluid was added and the cells were spun for 7 min at 1800 RPMs. The supernatant was decanted. The cell pellet was re-suspended in 2 mL of bovine sheath fluid and the cells were divided equally into seven appropriately labeled tubes. To each tube (not the unlabeled control or the original dead control), 0.1 mg of surface charged particles were added to each tube requiring particles. Samples were either incubated in a 34° C. water bath for 20 min or at room temperature for 20 min, to determine whether uptake of particles is facilitated at a higher temperature. After the incubation period had expired, the cell suspensions containing the particles and magnetically labeled cells were placed in a magnetic field. Once a magnetic pellet was collected, the nonmagnetic supernatant was aspirated and placed into another tube. Propidium iodide was added to the nonmagnetic fraction to label the dead and dying population to compare it to the original percent dead and dying cells that were not treated with particles. Cells were incubated with 100 µl of propidium iodide in the dark for 20 min and analyzed by a flow cytometer. The original dead percent was approximately 81% and was reduced to 15% using the magnetic particle treatment (FIG. 1A-1L).

Removal of dead and dying sperm from a fresh bull semen sample. One ejaculate was collected from each of three bulls. The ejaculate sperm concentration and volume were recorded and $640 \times 10^6$ cells per ejaculate were divided into four aliquots. Cells were gently centrifuged at 5000 RPMs for 6 min and the seminal plasma was aspirated from the pellet with a pipette. Each cell pellet was re-suspended in 4 mL of pre-warmed TRIS medium, so that the concentration of cells was 160×106 cells/mL. One mL of each re-suspended cell pellet was pipetted into four different 50 mL conical tubes: 1) control 34° C., 2) control RT, 3) particle treated 34° C., and 4) particle treated RT. To each treated sample, 100 µl of a 1.8 mg stock solution of net negative charged magnetic particles re-suspended in 600 µl of storage buffer (pH 7.4 PBS+0.1% BSA) was added and placed at the appropriate temperature for 20 min. After the 20 min incubation period had expired, for those samples containing particles, they were placed in front of a magnet for 1 min. The nonmagnetic fraction was aspirated out of the tube and placed into an eppendorf tube. From each sample after each magnetic separation was complete, aliquots were analyzed by flow cytometry for the dead percent prior to particle treatment as well as the dead percent after particle treatment. The average increase in viable sperm after the particle treatment was 18.7% (a change from an average of 74.68% viable to 93.38% viable after treatment). Optimal separation may occur once sperm that are susceptible have begun the process of capacitation and membrane alteration and have begun to die. This happens once the pH of the sperm has increased by at least 0.36 pH units (Vredenburgh-Wilberg, W. I. and Parrish, J. J. "Intracellular pH of Bovine Sperm Increases During Capacitation," Molecular Reproduction and Development 40:490-502, 1995).
Results:

| | | | | |
|---|---|---|---|---|
| Bull A Control 34° C. | 77.90% | Bull A Treated 34° C. | 94.90% |
| Bull A Control RT | 77.60% | Bull A Treated RT | 95.37% |
| Bull B Control 34° C. | 78.73% | Bull B Treated 34° C. | 98.70% |
| Bull B Control RT | 83.53% | Bull B Treated RT | 97.87% |
| Bull C Control 34° C. | 66.60% | Bull C Treated 34° C. | 88.43% |
| Bull C Control RT | 63.87% | Bull C Treated RT | 85.03% |

EXAMPLE 3

Removal of Damaged Sperm from Stallion Ejaculates

One ejaculate from each of three stallions was collected. Ejaculate sperm concentration was determined using a densimeter. Motility was determined objectively by a Sperm Vision CASA System (MiniTube, Verona, Wis., USA). The pH of the raw ejaculate was measured. Two aliquots of $160 \times 10^6$ total sperm were removed from each ejaculate from each stallion, representing control and treated samples. For control samples, sperm were immediately re-suspended in 1 mL of Modified Whitten's medium (pH 7.0) (Funahashi et al., 1996; Biology of Reproduction, 54:1412-1419) and held at room temperature. For particle treated sperm, $160 \times 10^6$ total sperm from each stallion were added to 1 mL of particles from a 3.6 mg/mL stock solution that had been collected and removed from a particle storage medium and suspended in 1 mL of Modified Whitten's medium in a 50-mL Falcon tube. The sperm/particle admixture was allowed to incubate at room temperature for 20 min. Following incubation, the tube was placed onto a magnet for 3 min. The non-magnetic fraction was removed by aspiration and transferred to a clean test tube. Total and progressive motility of the enriched sperm from each stallion was determined using the Sperm Vision CASA System and compared to the initial motility determinations.

All samples were then diluted to $25 \times 10^6$ progressively motile sperm/mL with E-Z Mixin® CST (Animal Reproduction Systems, Chino, Calif., USA) and allowed to cool to 5° C. for 24 h. Following the 24 h cooling period, samples were warmed to 37.5° C. for 10 min and assayed for total and progressive motility using the Sperm Vision CASA System.
Results:

| | 0-h Total Motility % | 0-h Progressive Motility % | 24-h Cooled Total Motility % | 24-h Cooled Progressive Motility % |
|---|---|---|---|---|
| Stallion A Ejaculate pH: 6.91 | | | | |
| Control | 78 | 59 | 50 | 45 |
| Treated | 88 | 73 | 60 | 50 |
| Stallion B Ejaculate pH: 6.96 | | | | |
| Control | 61 | 48 | 11 | 6 |
| Treated | 65 | 51 | 26 | 22 |
| Stallion C Ejaculate pH: 7.40 | | | | |
| Control | 75 | 72 | 53 | 47 |
| Treated | 88 | 82 | 61 | 58 |

OVERALL RESULTS

| | N | 0-h Total Motility % | 0-h Progressive Motility % | 24-h Cooled Total Motility % | 24-h Cooled Progressive Motility % |
|---|---|---|---|---|---|
| Control | 3 | 71.3 | 59.7 | 38 | 32.7 |
| Treated | 3 | 80.3 | 68.7 | 49 | 43.3 |

The removal of damaged/dead sperm from a fresh ejaculate, followed by extending and cooling sperm for 24 h resulted in an increase in both total and progressive motile sperm in each treated sample compared to controls. The overall improvement in motility scores from treated samples was observed at both the 0 h (prior to cooling) and post-cool 24 h period.

EXAMPLE 4

Removal of Damaged Sperm from Stallion Ejaculates Prior to Cryopreservation

On day 1, a single ejaculate was collected from each of two stallions and divided into two aliquots, one for the untreated control and the other for the particle treated sample. The neat semen was immediately diluted 1:1 with Modified Whitten's medium. The diluted samples were centrifuged for 7 min to remove the seminal plasma. The supernatant was immediately aspirated and discarded. The sperm pellet was suspended and sperm concentration was obtained. The untreated control aliquots were re-suspended to $40 \times 10^6$ cells/mL in a French egg yolk/milk extender containing 5% glycerol. Control sperm were cooled for 2 h at 5° C., packaged in 0.5 mL straws, and frozen over liquid nitrogen vapor. To the treated aliquots, 1:1 mL of particles (3.6 mg/mL) re-suspended in Modified Whitten's medium was added to $160 \times 10^6$ total sperm contained in 500 μL of Modified Whitten's medium. Treated samples were allowed to incubate with the particles for 20 min at room temperature. Following particle exposure time to the sperm, the particles were magnetically collected and the nonmagnetic fraction was aspirated and dispensed into a separate tube. Treated samples for both stallions were extended to a total of 4 mL with a French egg yolk/milk extender containing 5% glycerol. Treated sperm were allowed to cool for 2 h at 5° C., and were packaged in 0.5 mL straws and frozen over liquid nitrogen.

On day 2, a single ejaculate was collected from each of two stallions and each ejaculate was divided into two aliquots: untreated control and particle treated. The neat semen was diluted 1:1 with Modified Whitten's medium, and centrifuged for 9 min. The seminal plasma was aspirated and discarded. For both control and treated samples, $80 \times 10^6$ total sperm were deposited into 275 μL Whitten's medium. Control samples were extended to $40 \times 10^6$ sperm/mL in a total of 2 mL with EZ Freezin-LE (Animal Reproduction Systems) a prepackaged Lactose/EDTA freezing extender containing 5% glycerol. Treated samples were allowed to incubate with the particles for 20 min at room temperature. After the incubation period had expired, magnetically labeled cells were collected on a magnet and the nonmagnetic cells were aspirated and placed in another tube. Treated samples were re-suspended to $40 \times 10^6$ sperm/mL in a total of 2 mL with EZ Freezin-LE. Extended semen from each stallion/treatment was packaged in 0.5 mL straws and placed on a freezing rack. The freezing rack was placed inside of a styrofoam box containing a known depth of liquid nitrogen so that the straws were in the vapor phase of the nitrogen and the lid was loosely placed over the top of the box.

Results:

| | CONTROL (%) | | | | TREATED (%) | | | |
|---|---|---|---|---|---|---|---|---|
| Stallion | Total Motility | Progressive Motility | Live | Dead | Total Motility | Progressive Motility | Live | Dead |
| Sammy | 5 | 2 | 22 | 78 | 45 | 30 | 70 | 30 |
| Gunsmoke | 15 | 5 | 14 | 86 | 40 | 10 | 75 | 25 |
| Tinman | 62 | 22 | 56 | 44 | 67 | 26 | 73 | 27 |
| Scotti | 62 | 34 | 50 | 50 | 58 | 33 | 54 | 46 |

| MEAN 0-h TOTAL AND PROGRESSIVE MOTILITY (%) and Live/Dead (%) | | | | |
|---|---|---|---|---|
| | Total Motility | Progressive Motility | Live | Dead |
| Control | 36 | 16 | 36 | 64 |
| Treated | 52 | 25 | 68 | 32 |

N = 4 Stallions

Removal of damaged/dead stallion sperm prior to cryopreservation increased 0 h post-thaw total and progressive motility by 44% and 62% respectively, compared to control sperm. The percentage of viable sperm immediately after thawing was increased 32 percentage points or 89% when dead and/or damaged sperm were removed prior to cryopreservation. Removal of compromised sperm prior to cryopreservation increased overall sperm quality.

Zeta potential measurements of carboxyl group containing silane coated magnetic particles in buffers such as TRIS, TALP, dH$_2$O, and storage buffer were measured by a zeta sizer and the resulting net zeta potential is shown in FIGS. 2A-7F. Particles with carboxyl silane coating in this example measure as a net negative zeta potential in each buffer condition and may be expected to bind to sperm having undergone or undergoing capacitation and losing the net negative charge seen in viable sperm.

Parameters for FIGS. 1A-1C:

| Quadrant Statistics | | | |
|---|---|---|---|
| File: | unstaned.001 | Log Data Units: | Linear Values |
| Sample ID: | unstained | Patient ID: | |
| Tube: | Untitled | Panel: | Untitled Acquisition Tube List |
| Acquisition Date: | 09-Dec-11 | Gate: | G1 |
| Gated Events | 1000 | Total Events: | 12962 |
| X Parameter: | FL1-H (Log) | Y Parameter: | FL2-H (Log) |
| Quad location: | 9, 14 | | |

| Quad | Events | % Gated | % Total | X Mean | X Geo Mean | Y Mean | Y Mean |
|---|---|---|---|---|---|---|---|
| UL | 3 | 0.03 | 0.02 | 7.17 | 7.13 | 17.80 | 17.78 |
| UR | 1 | 0.01 | 13.95 | 13.95 | 29.96 | 29.96 | |
| LL | 9996 | 99.96 | 77.18 | 2.76 | 2.59 | 3.22 | 2.88 |
| LR | 0 | 0.00 | 0.00 | *** | *** | *** | *** |

Figure 1D:
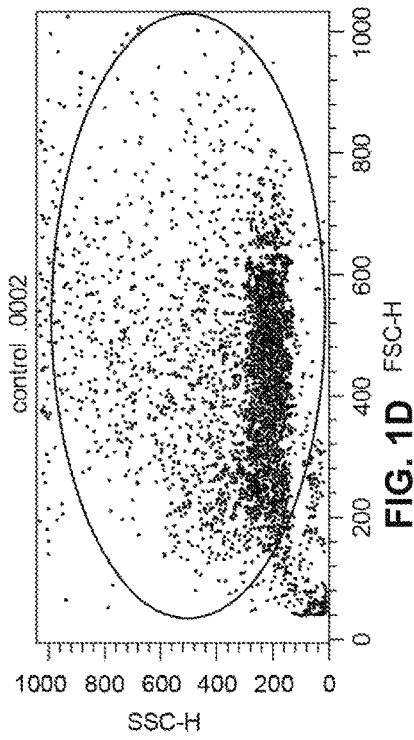
FIG. 1D shows flow cytometry analysis of an ejaculate sample before example magnetic particle treatment, labeled with propidium iodide, plotted as side light scatter (SSC-H) as a function of forward light scatter (FSC-H) measurements.
Figure 1F:
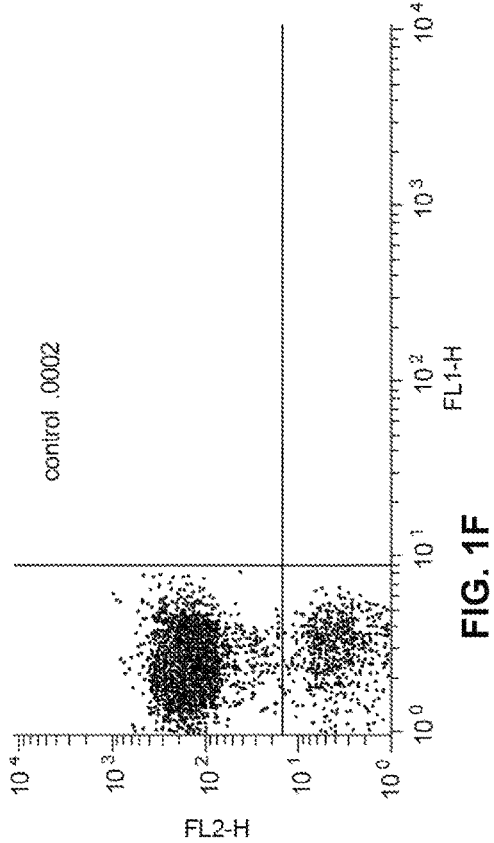
FIG. 1F shows flow cytometry analysis of an ejaculate sample before example magnetic particle treatment, labeled with propidium iodide, plotted as a two-parameter dot plot of two fluorescence height measurements, FL2-H and FL1-H.

Parameters for FIGS. 1D-1F:

| Quadrant Statistics | | | |
|---|---|---|---|
| File: | unstaned.001 | Log Data Units: | Linear Values |
| Sample ID: | unstained | Patient ID: | |
| Tube: | Untitled | Panel: | Untitled Acquisition Tube List |
| Acquisition Date: | 09-Dec-11 | Gate: | G1 |
| Gated Events | 1000 | Total Events: | 12962 |
| X Parameter: | FL1-H (Log) | Y Parameter: | FL2-H (Log) |
| Quad location: | 9, 14 | | |

| Quad | Events | % Gated | % Total | X Mean | X Geo Mean | Y Mean | Y Mean |
|---|---|---|---|---|---|---|---|
| UL | 8132 | 81.32 | 69.70 | 2.73 | 2.59 | 143.93 | 131.70 |
| UR | 4 | 0.04 | 0.05 | 15.06 | 13.04 | 128.51 | 120.79 |
| LL | 1863 | 16.63 | 15.97 | 3.02 | 2.83 | 3.57 | 3.35 |
| LR | 1 | 0.01 | 0.01 | 9.82 | 9.82 | 9.22 | 9.22 |

Figure 1H:
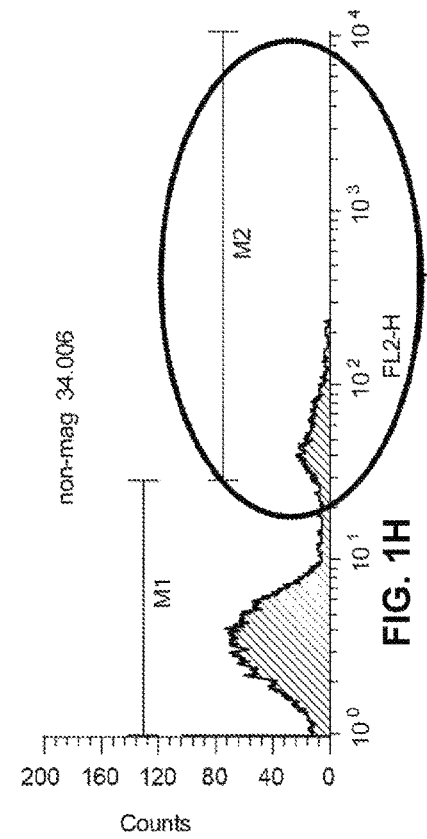
FIG. 1H shows flow cytometry analysis of an ejaculate sample with particles but before magnetic treatment at 34° C., plotted as fluorescence height (FL2-H) in counts, showing dead particle treated cells (M2, 14.73%) and live particle treated cells (M1, 85.27%)
Figure 1G:
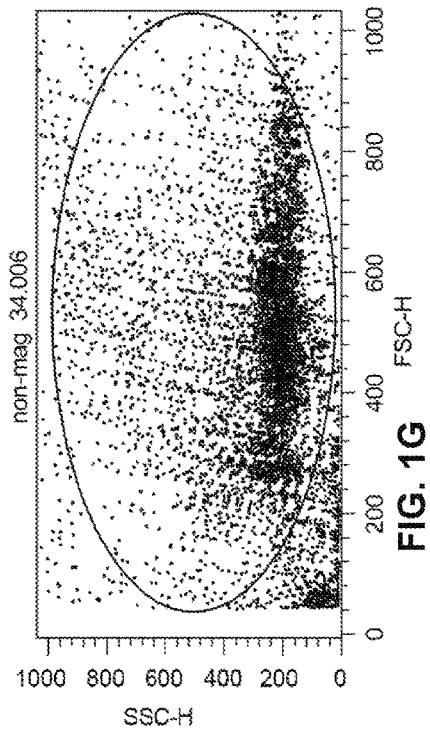
FIG. 1G shows flow cytometry analysis of an ejaculate sample with particles but before magnetic treatment at 34° C., plotted as side light scatter (SSC-H) as a function of forward light scatter (FSC-H) measurements.
Figure 1I:
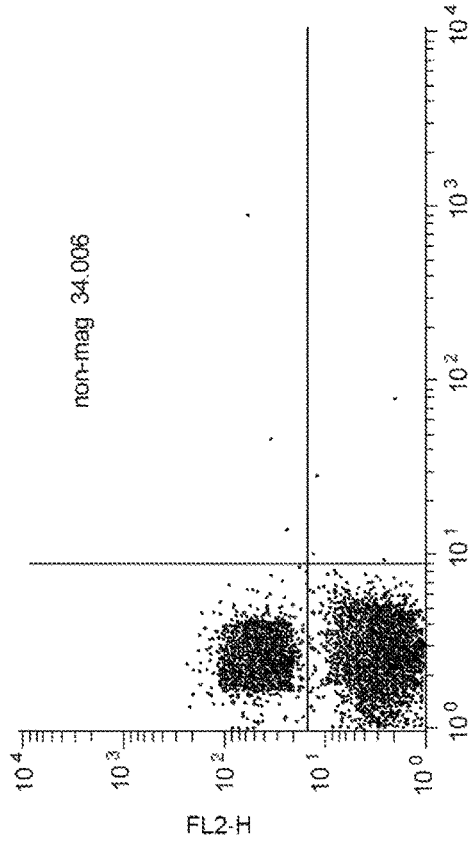
FIG. 1I shows flow cytometry analysis of an ejaculate sample with particles but before magnetic treatment at 34° C., plotted as a two-parameter dot plot of two fluorescence height measurements, FL2-H and FL1-H.

Parameters for FIGS. 1G-1I

| Quadrant Statistics | | | |
|---|---|---|---|
| File: | non-mag 34.006 | Log Data Units: | Linear Values |
| Sample ID: | non-mag 34 | Patient ID: | |
| Tube: | Untitled | Panel: | Untitled Acquisition Tube List |
| Acquisition Date: | 9 Dec. 2011 | Gate: | G1 |
| Gated Events | 1000 | Total Events: | 31123 |
| X Parameter: | FL1-H (Log) | Y Parameter: | FL2-H (Log) |
| Quad location: | 9, 14 | | |

| Quad | Events | % Gated | % Total | X Mean | X Geo Mean | Y Mean | Y Mean |
|---|---|---|---|---|---|---|---|
| UL | 1473 | 14.73 | 4.70 | 2.98 | 2.74 | 49.18 | 43.42 |
| UR | 3 | 0.03 | 0.01 | 319.23 | 82.54 | 34.20 | 29.60 |
| LL | 8516 | 85.16 | 27.36 | 2.93 | 2.64 | 3.87 | 3.38 |
| LR | 8 | 0.06 | 0.03 | 21.04 | 14.19 | 7.42 | 6.31 |

Figure 1K:
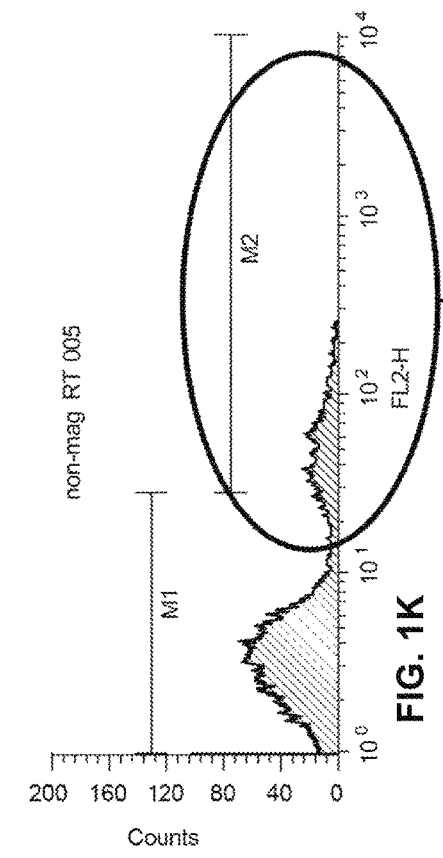
FIG. 1K shows flow cytometry analysis of an ejaculate sample with particles but before magnetic treatment at 25° C., plotted as fluorescence height (FL2-H) in counts, showing dead particle treated cells (M2, 18.32%) and live particle treated cells (M1, 81.68%)
Figure 1J:
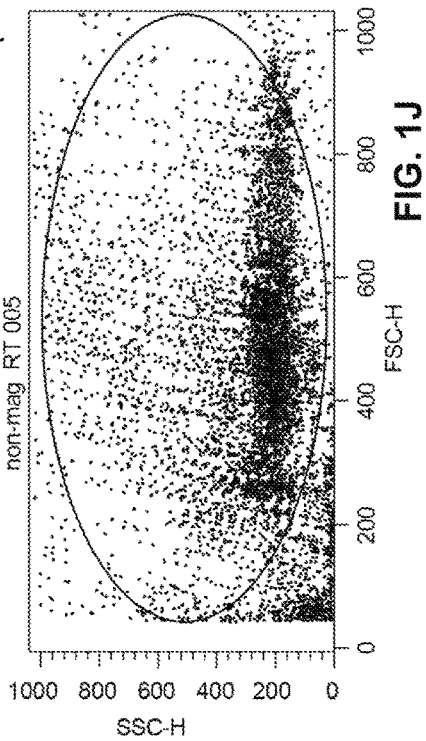
FIG. 1J shows flow cytometry analysis of an ejaculate sample with particles but before magnetic treatment at 25° C., plotted as side light scatter (SSC-H) as a function of forward light scatter (FSC-H) measurements.
Figure 1L:
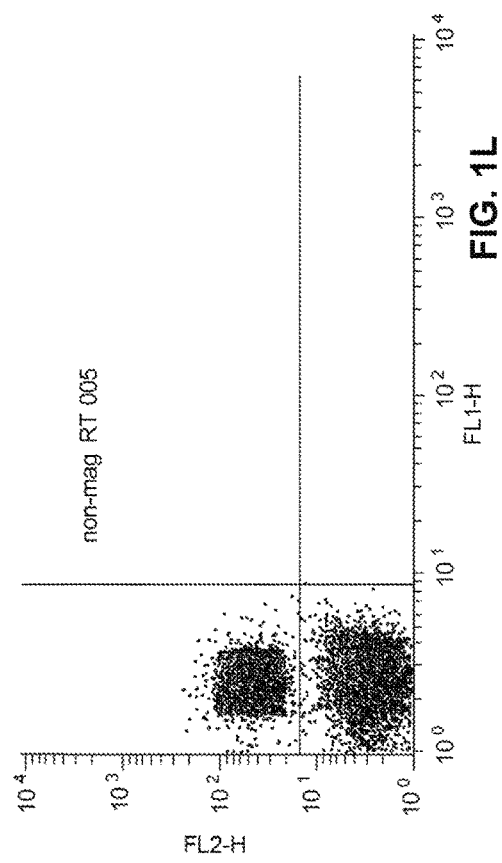
FIG. 1L shows flow cytometry analysis of an ejaculate sample with particles but before magnetic treatment at 25° C., plotted as a two-parameter dot plot of two fluorescence height measurements, FL2-H and FL1-H.

Parameters for FIGS. 1J-1L

| Quadrant Statistics | | | |
|---|---|---|---|
| File: | non-mag RT.005 | Log Data Units: | Linear Values |
| Sample ID: | non-mag RT | Patient ID: | |
| Tube: | Untitled | Panel: | Untitled Acquisition Tube List |
| Acquisition Date: | 9 Dec. 2011 | Gate: | G1 |
| Gated Events | 1000 | Total Events: | 31123 |
| X Parameter: | FL1-H (Log) | Y Parameter: | FL2-H (Log) |
| Quad location: | 9, 14 | | |

| Quad | Events | % Gated | % Total | X Mean | X Geo Mean | Y Mean | Y Mean |
|---|---|---|---|---|---|---|---|
| UL | 1832 | 18.32 | 6.26 | 2.65 | 2.52 | 52.41 | 45.04 |
| UR | 0 | 0.00 | 0.00 | *** | *** | *** | *** |
| LL | 8168 | 81.68 | 27.92 | 2.70 | 2.42 | 3.63 | 3.12 |
| LR | 0 | 0.00 | 0.00 | *** | *** | *** | *** |

Figure 2A:
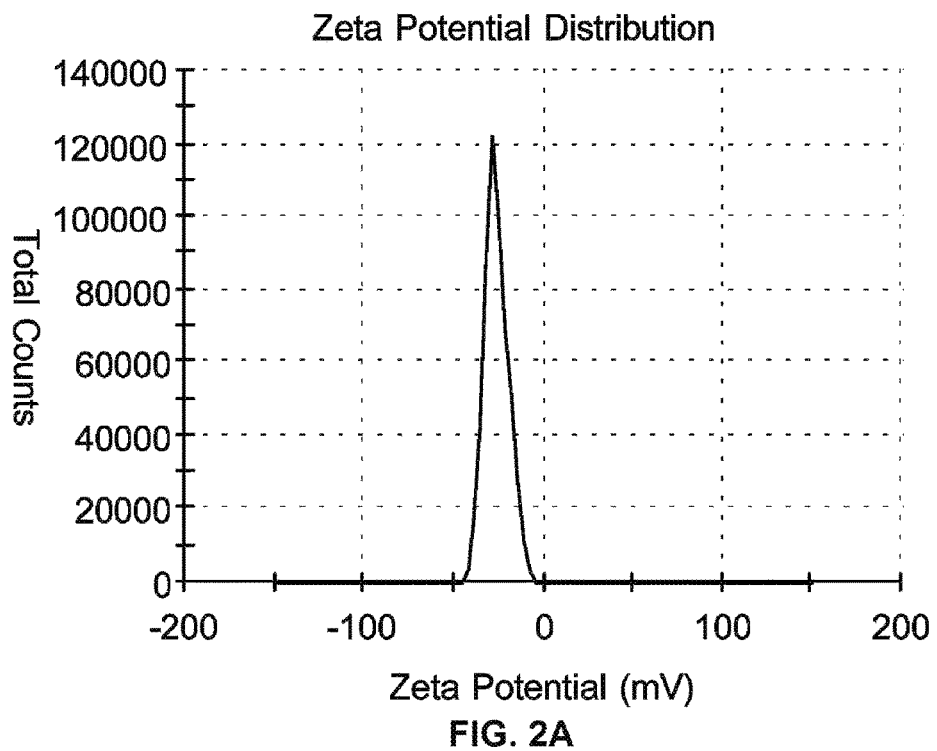
FIG. 2A shows zeta potential analysis details of example particles described herein as re-suspended in storage buffer at −28.2 mV.
Figure 2B:
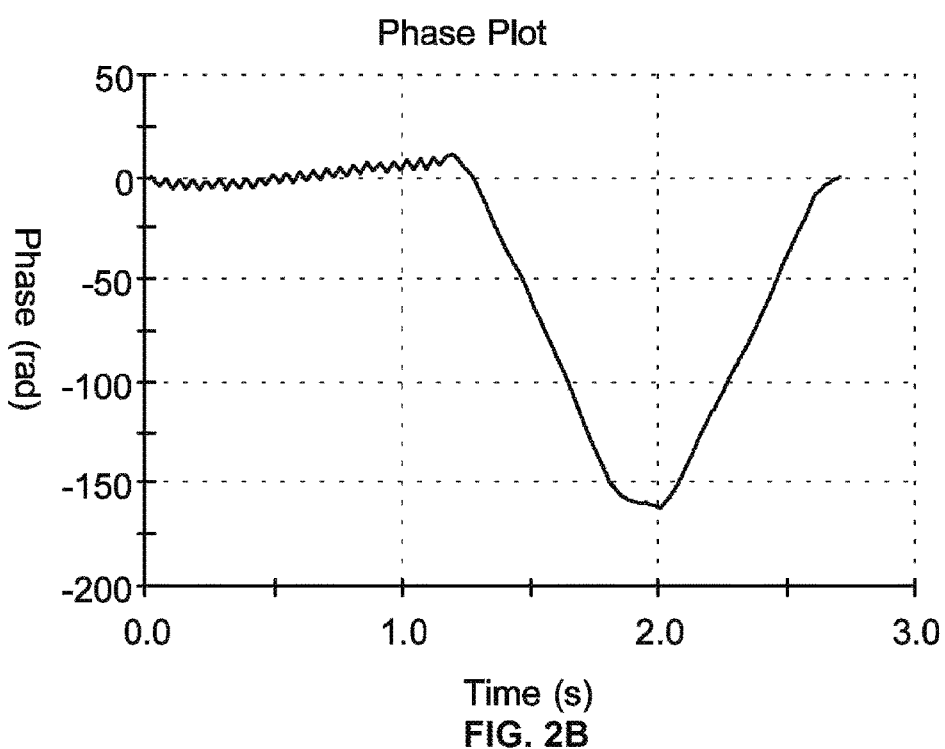
FIG. 2B shows zeta potential analysis details of example particles described herein as re-suspended in storage buffer at −28.2 mV, as a plot of phase versus time in seconds.

Parameters for FIGS. 2A and 2B

| Measurement Details | | | |
|---|---|---|---|
| Sample Name | Lot-103011 1:10 Zeta 3 | Temperature (C. °): | 29.0 |
| Dispersant Name: | Water | Count Rate (kcps): | 163.5 |
| Viscosity (cP): | 0.8096 | Zeta Runs: | 12 |
| Dispersant RI: | 1.330 | Attenuator: | 6 |

| Monomodal Analysis Results | | | |
|---|---|---|---|
| Result Quality: | Good | Mobility (μmcm/Vs): | −2.383 |
| Zeta Potential (mV): | −28.2 | Standard Deviation (μmcm/Vs): | 1.876 |
| Standard Deviation (mV): | 22.2 | Conductivity (mS/cm): | 2.48 |
| Quality Factor: | 3.15 | | |

| Multimodal Distribution | | |
|---|---|---|
| | Mean (mv) | Area (%) | Width (mV) |
| Peak 1: | −26.1 | 100.0 | 6.52 |
| Peak 2: | 0.00 | 0.00 | 0.00 |
| Peak 3: | 0.00 | 0.00 | 0.00 |

Figure 3A:
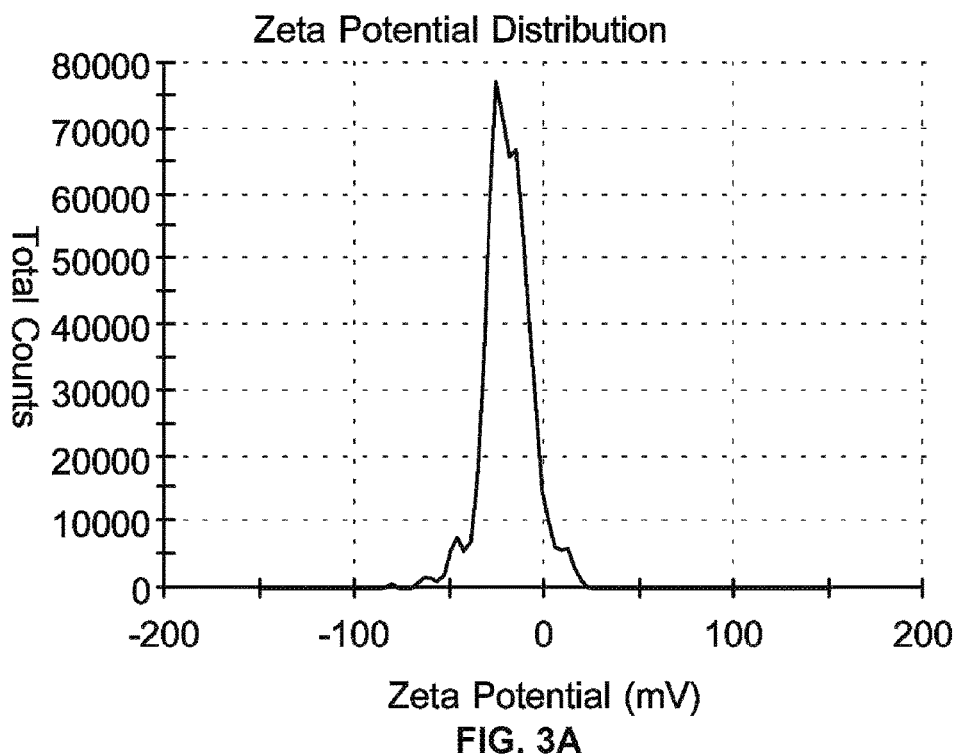
FIG. 3A shows zeta potential analysis details of example particles described herein as re-suspended in storage buffer at −22.4 mV.
Figure 3B:
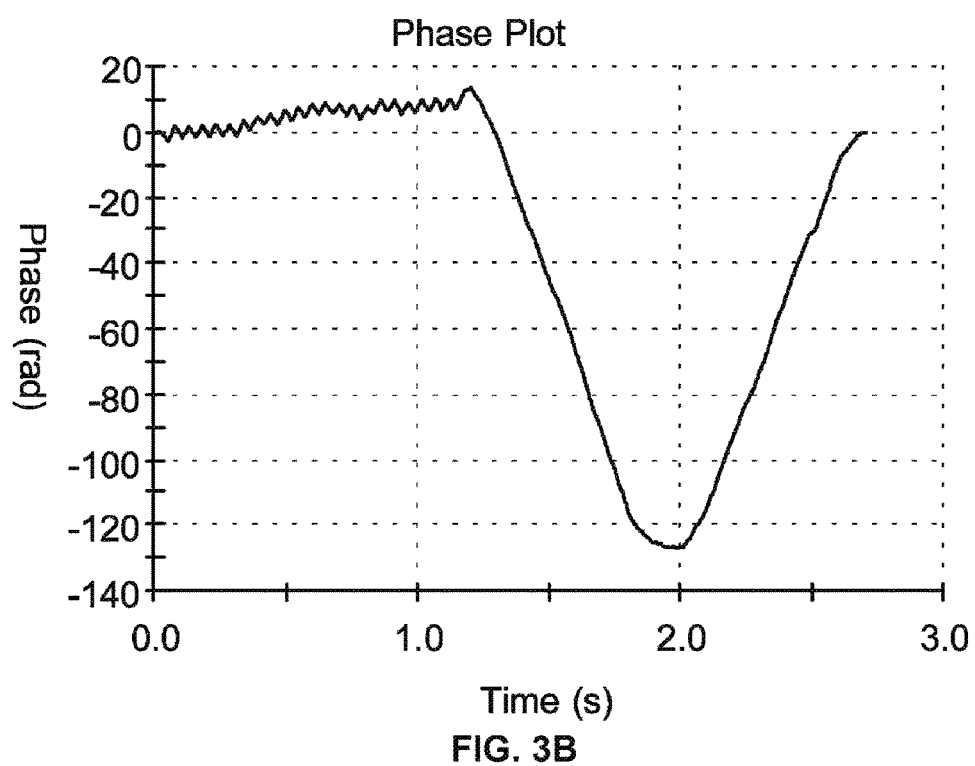
FIG. 3B shows zeta potential analysis details of example particles described herein as re-suspended in storage buffer at −22.4 mV, as a plot of phase versus time in seconds.

Parameters for FIGS. 3A and 3B

| Measurement Details | | | |
|---|---|---|---|
| Sample Name | Lot-103011 1:10 Zeta 4 | Temperature (C. °): | 29.0 |
| Dispersant Name: | Water | Count Rate (kcps): | 164 |
| Viscosity (cP): | 0.8096 | Zeta Runs: | 12 |
| Dispersant RI: | 1.330 | Attenuator: | 6 |

-continued

| Monomodal Analysis Results | | | |
|---|---|---|---|
| Result Quality: | — | Mobility (μmcm/Vs): | −1.891 |
| Zeta Potential (mV): | −22.4 | Standard Deviation (μmcm/Vs): | 2.354 |
| Standard Deviation (mV): | 27.9 | Conductivity (mS/cm): | 2.54 |
| Quality Factor: | 1.45 | | |

| Multimodal Distribution | | | |
|---|---|---|---|
| | Mean (mv) | Area (%) | Width (mV) |
| Peak 1: | −25.8 | 49.6 | 5.73 |
| Peak 2: | −11.1 | 0.00 | 6.77 |
| Peak 3: | −47.3 | 3.4 | 3.83 |

Figure 4A:
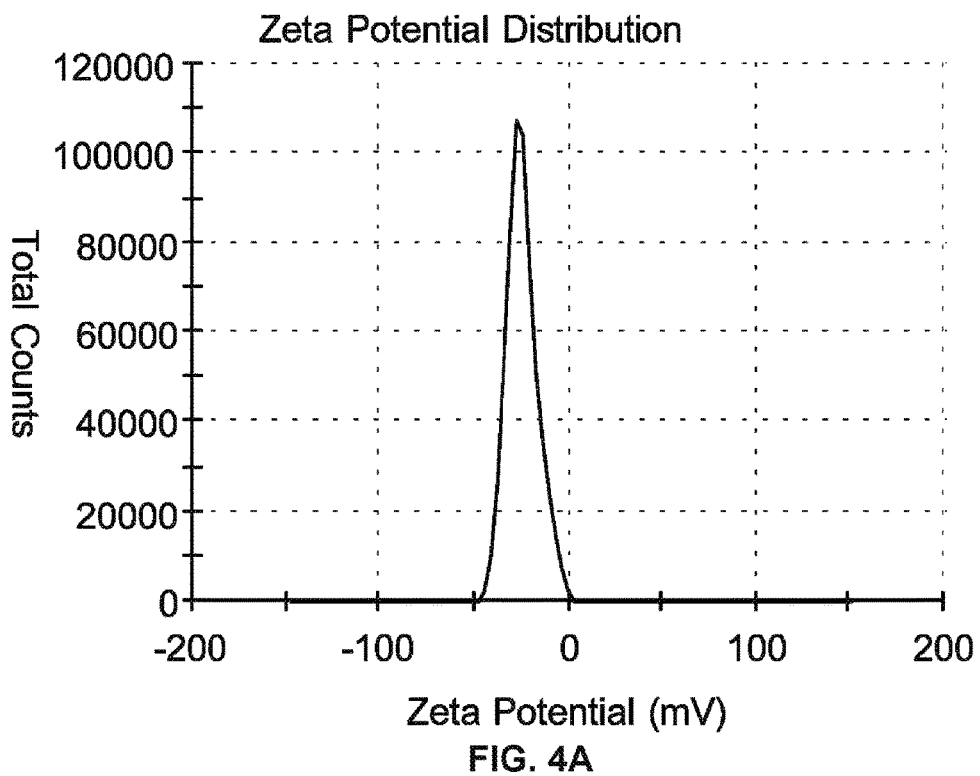
FIG. 4A shows zeta potential analysis details of example particles described herein as re-suspended in TALP buffer at −24.6 mV.
Figure 4B:
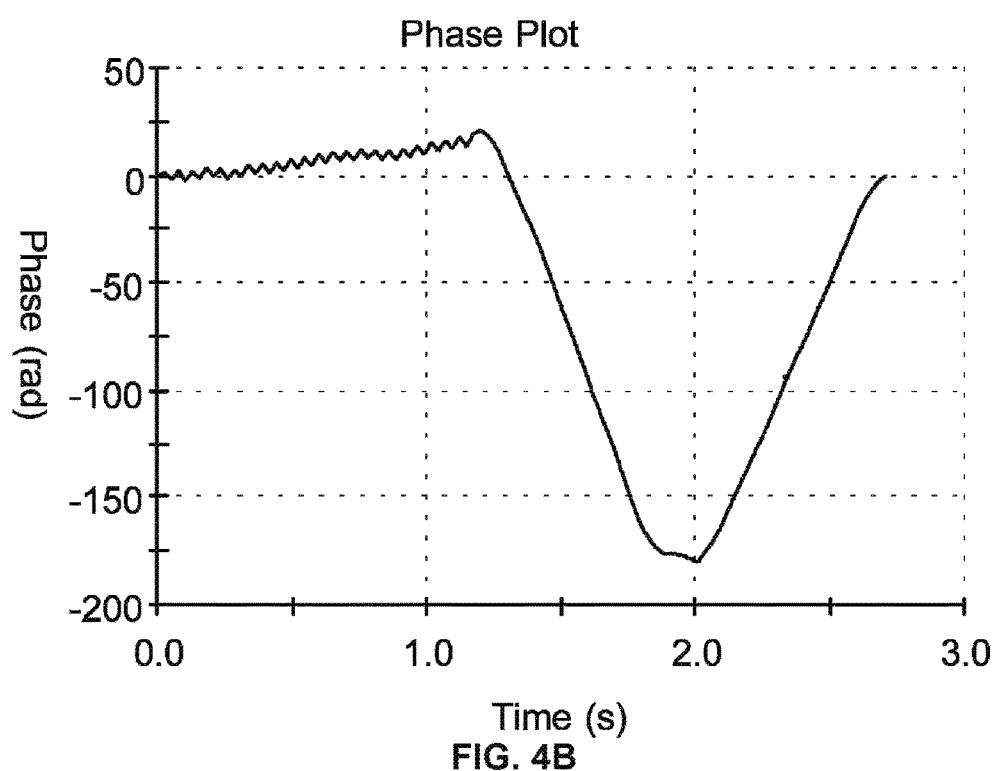
FIG. 4B shows zeta potential analysis details of example particles described herein as re-suspended in TALP buffer at −24.6 mV, as a plot of phase versus time in seconds.

Parameters for FIGS. 4A and 4B

| Measurement Details | | | |
|---|---|---|---|
| Sample Name | Lot-043012-A TALP buffer 1:10 Z . . . | Temperature (C. °): | 29.0 |
| Dispersant Name: | Water | Count Rate (kcps): | 183.1 |
| Viscosity (cP): | 0.8096 | Zeta Runs: | 12 |
| Dispersant RI: | 1.330 | Attenuator: | 7 |

| Monomodal Analysis Results | | | |
|---|---|---|---|
| Result Quality: | Good | Mobility (μmcm/Vs): | −2.074 |
| Zeta Potential (mV): | −24.6 | Standard Deviation (μmcm/Vs): | 0.6904 |
| Standard Deviation (mV): | 8.18 | Conductivity (mS/cm): | 1.80 |
| Quality Factor: | 3.54 | | |

| Multimodal Distribution | | | |
|---|---|---|---|
| | Mean (mv) | Area (%) | Width (mV) |
| Peak 1: | −24.6 | 100 | 8.18 |
| Peak 2: | 0.00 | 0.00 | 0.00 |
| Peak 3: | 0.00 | 0.00 | 0.00 |

Figure 5A:
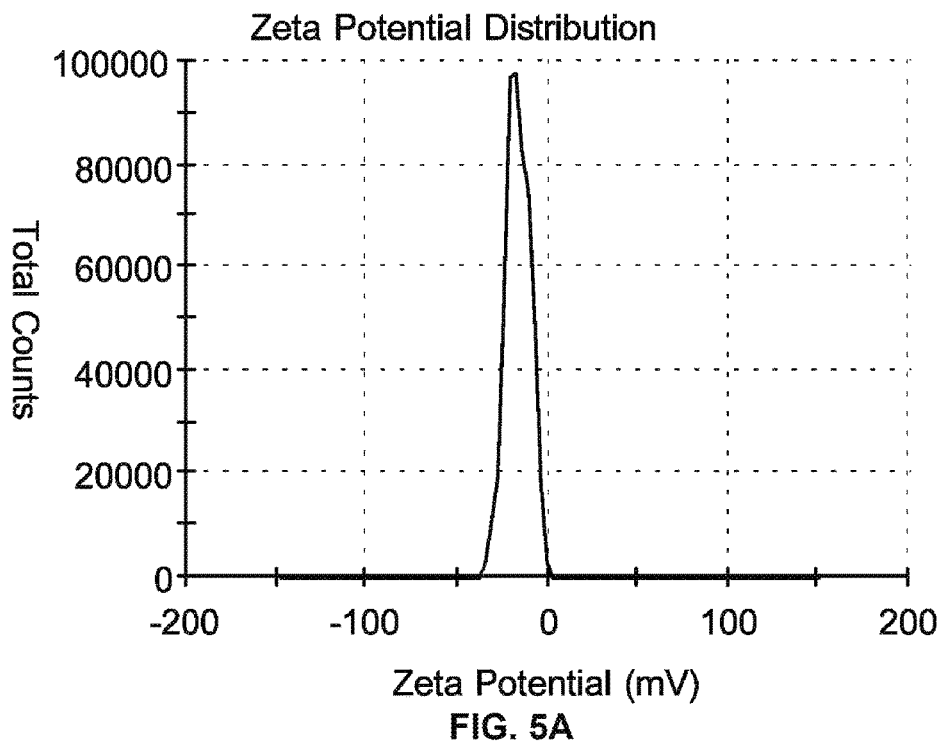
FIG. 5A shows zeta potential analysis details of example particles described herein as re-suspended in MES buffer at −16.5 mV.
Figure 5B:
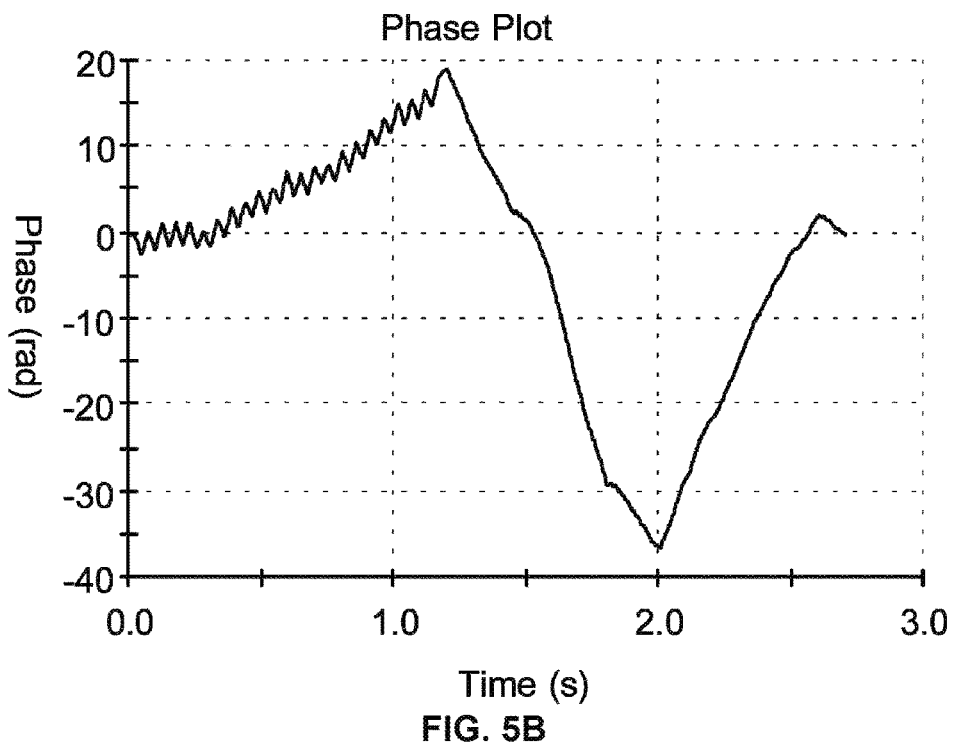
FIG. 5B shows zeta potential analysis details of example particles described herein as re-suspended in MES buffer at −16.5 mV, as a plot of phase versus time in seconds.

Parameters for FIGS. 5A and 5B

| Measurement Details | | | |
|---|---|---|---|
| Sample Name | Lot-043012-A MRS buffer 1:10 Z . . . | Temperature (C. °): | 29.0 |
| Dispersant Name: | Water | Count Rate (kcps): | 146.5 |
| Viscosity (cP): | 0.8096 | Zeta Runs: | 12 |
| Dispersant RI: | 1.330 | Attenuator: | 6 |

| Monomodal Analysis Results | | | |
|---|---|---|---|
| Result Quality: | Good | Mobility (μmcm/Vs): | −1.392 |
| Zeta Potential (mV): | −16.5 | Standard Deviation (μmcm/Vs): | 0.5526 |
| Standard Deviation (mV): | 6.55 | Conductivity (mS/cm): | 2.28 |
| Quality Factor: | 3.74 | | |

| Multimodal Distribution | | | |
|---|---|---|---|
| | Mean (mv) | Area (%) | Width (mV) |
| Peak 1: | −16.5 | 100 | 6.55 |
| Peak 2: | 0.00 | 0.00 | 0.00 |
| Peak 3: | 0.00 | 0.00 | 0.00 |

Figure 6A:
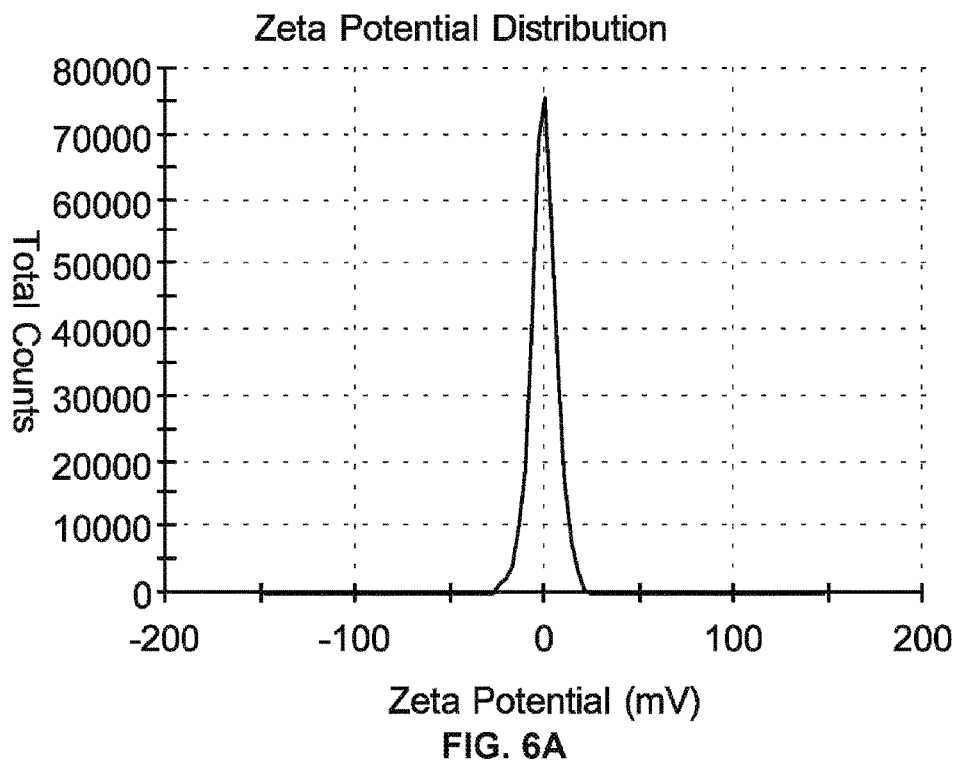
FIG. 6A shows zeta potential analysis details of example particles described herein as re-suspended in dH2O −26.6 mV.
Figure 6B:
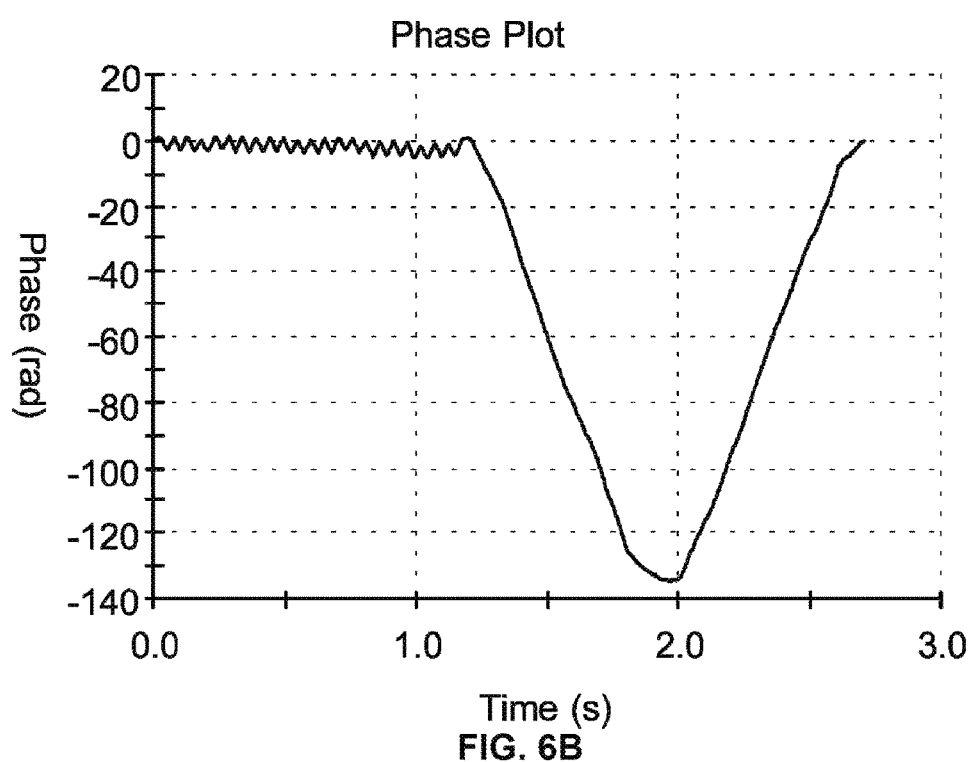
FIG. 6B shows zeta potential analysis details of example particles described herein as re-suspended in dH2O −26.6 mV, as a plot of phase versus time in seconds.

Parameters for FIGS. 6A and 6B

| Measurement Details | | | |
|---|---|---|---|
| Sample Name | Lot-043012-A dH20 1:10 Zeta 2 | Temperature (C. °): | 29.0 |
| Dispersant Name: | Water | Count Rate (kcps): | 70.4 |
| Viscosity (cP): | 0.8096 | Zeta Runs: | 12 |
| Dispersant RI: | 1.330 | Attenuator: | 6 |
| Monomodal Analysis Results | | | |
| Result Quality: | Good | Mobility (μmcm/Vs): | −2.244 |
| Zeta Potential (mV): | −26.6 | Standard Deviation (μmcm/Vs): | 6.039 |
| Standard Deviation (mV): | 71.6 | Conductivity (mS/cm): | 0.0331 |
| Quality Factor: | 2.31 | | |

| Multimodal Distribution | | | |
|---|---|---|---|
| | Mean (mv) | Area (%) | Width (mV) |
| Peak 1: | −0.594 | 100 | 6.89 |
| Peak 2: | 0.00 | 0.0 | 0.00 |
| Peak 3: | 0.00 | 0.0 | 0.00 |

Figure 7A:
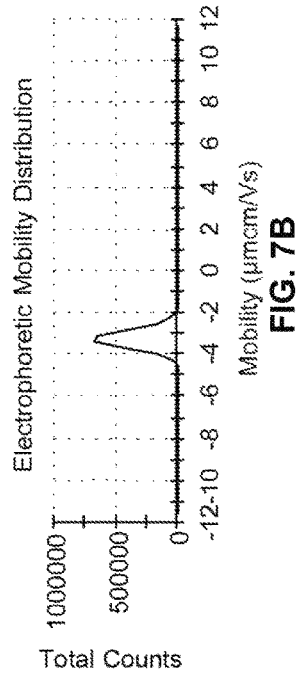
FIG. 7A shows zeta potential analysis details of example particles described herein as re-suspended in TRIS buffer at −42.4 mV.
Figure 7B:
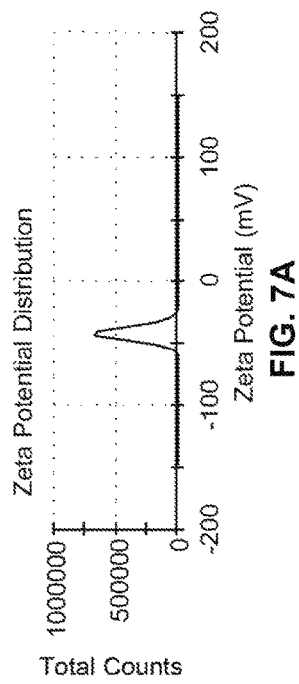
FIG. 7B shows zeta potential analysis details of example particles described herein as re-suspended in TRIS buffer at −42.4 mV, plotted as mobility in μmem/Vs.
Figure 7C:
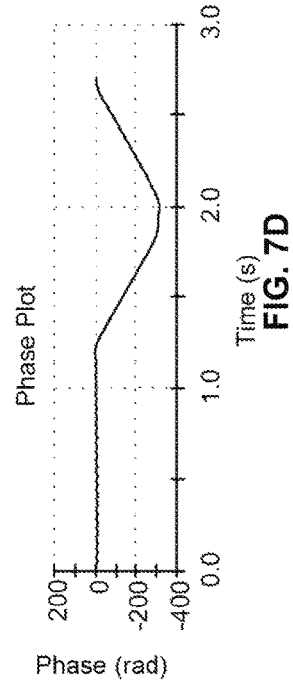
FIG. 7C shows zeta potential analysis details of example particles described herein as re-suspended in TRIS buffer at −42.4 mV, plotted as frequency shift in Hz.
Figure 7D:
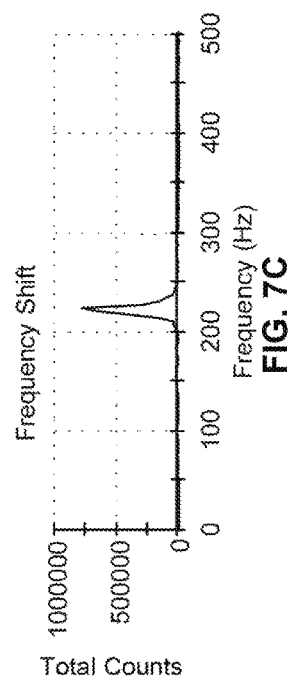
FIG. 7D shows zeta potential analysis details of example particles described herein as re-suspended in TRIS buffer at −42.4 mV, as a plot of phase versus time in seconds.
Figure 7E:
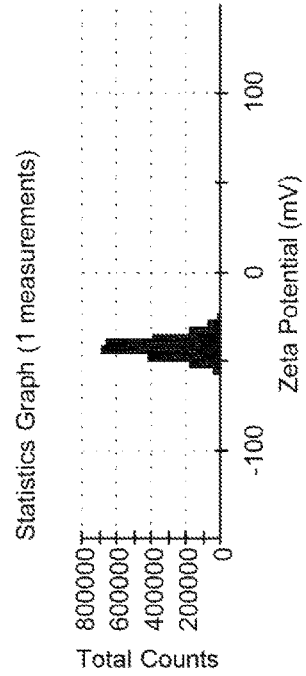
FIG. 7E shows zeta potential analysis details of example particles described herein as re-suspended in TRIS buffer at −42.4 mV, plotted as zeta potential voltage and current versus time in seconds.
Figure 7F:
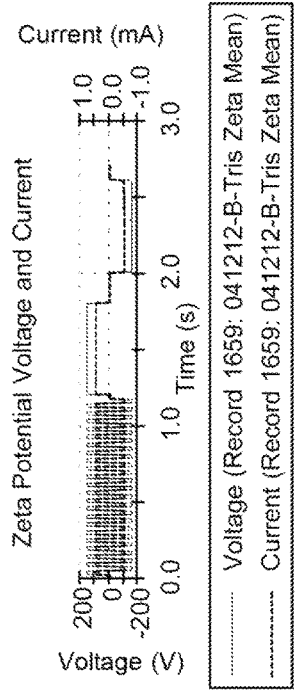
FIG. 7F shows zeta potential analysis details of example particles described herein as re-suspended in TRIS buffer at −42.4 mV, plotted as a histogram.

Parameters for FIGS. 7A and 7F

| Sample Details | | | |
|---|---|---|---|
| Sample Name: | 041212-B-Tris Zeta Mean | | |
| SOP Name: | Zeta standard 3 × 20 25C no wait.sop | | |
| File Name | 2012-01020 new measure . . . | Dispersant Name: | Water |
| Record Number | 1659 | Dispersant RI: | 1.330 |
| Measurement Date and Time: | Friday, Apr. 20, 2012 2:550:0 | Viscosity (cP): | 0.8872 |
| System | | | |
| Temperature (C. °): | 25.0 | Zeta Runs: | 20 |
| Count Rate (kcps): | 2456.7 | Measurement Position (mm): | 2.00 |
| Cell Description: | Clear disposable zeta cell | Attenuator: | 9 |
| Results | | | |
| | Result Quality: | Good | |
| | Zeta Potential (mV): | −42.2 | |
| | Zeta SD (mV): | 5.70 | |
| | Mobility (μmcm/Vs): | −3.307 | |
| | Mobility SD (μmcm/Vs): | 0.4464 | |
| | Wall Zeta Potential (mV): | −47.9 | |
| | Effective Voltage (V): | 151 | |
| | Conductivity (mS/cm): | 0.240 | |

| | Mean (mv) | Area (%) | Width (mV) |
|---|---|---|---|
| Peak 1: | −42.2 | 100 | 5.64 |
| Peak 2: | 0.00 | 0.00 | 0.00 |
| Peak 3: | 0.00 | 0.00 | 0.00 |

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range may be easily recognized as sufficiently describing and enabling the same range being broken down into at least equal halves, thirds, quarters, fifths, tenths, and the like. As a non-limiting example, each range discussed herein may be readily broken down into a lower third, middle third and upper third, and the like. As will also be understood by one skilled in the art all language such as "up to," "at least," "greater than," "less than," include the number recited and refer to ranges which may be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A method of separating viable sperm from dead or damaged sperm comprising:
    diluting a semen sample comprising viable sperm, and dead or damaged sperm, with a buffered media;
    adding magnetic particles to the diluted semen sample to form an admixture, wherein each magnetic particle is no greater than 1000 nm and coated with a chargeable silicon-containing compound and a chargeable silicon-containing compound;
    binding a portion of the dead or damaged sperm to the magnetic particles in the diluted admixture through an electrical charge interaction; and
    magnetically separating the bound dead or damaged sperm from unbound viable sperm.

2. The method of claim 1, wherein the magnetic particles comprise $Fe_3O_4$.

3. The method of claim 1, wherein the magnetic particles comprise 2-(carbomethoxy)ethyltrimethoxysilane.

4. The method of claim 1, wherein each magnetic particle is between 30 nm to 1000 nm in size.

5. The method of claim 1, further comprising the step of centrifuging the semen sample prior to the step of adding the magnetic particles.

6. The method of claim 5, further comprising the step of decanting the centrifuged semen sample.

7. The method of claim 6, further comprising the step of resuspending the centrifuged semen sample in buffered media.

* * * * *